(12) United States Patent
Bridger et al.

(10) Patent No.: US 6,756,391 B2
(45) Date of Patent: Jun. 29, 2004

(54) ANTIVIRAL COMPOUNDS

(75) Inventors: Gary James Bridger, Bellingham, WA (US); Eva Maria Boehringer, Vancouver (CA); Zhongren Wang, West Chester, PA (US); Dominique Schols, Herent (BE); Renato Tony Skerlj, Vancouver (CA); David Earl Bogucki, Surrey (CA)

(73) Assignee: AnorMed, Inc., Langley (CA)

( * ) Notice: Subject to any disclaimer, the term of this patent is extended or adjusted under 35 U.S.C. 154(b) by 0 days.

(21) Appl. No.: 10/143,692

(22) Filed: May 9, 2002

(65) Prior Publication Data

US 2003/0018189 A1 Jan. 23, 2003

Related U.S. Application Data

(63) Continuation of application No. 09/111,895, filed on Jul. 8, 1998, now Pat. No. 6,506,770, which is a continuation-in-part of application No. 08/659,500, filed on Jun. 6, 1996, now Pat. No. 5,817,807.

(30) Foreign Application Priority Data

Jun. 6, 1995 (GB) .............................................. 9511357

(51) Int. Cl.$^7$ ...................... A61K 31/675; A61K 31/44; A61K 31/33; A61P 31/12; C07D 243/14

(52) U.S. Cl. .......................... 514/338; 514/79; 514/85; 514/86; 514/89; 514/94; 514/183; 514/252.13; 514/255.05; 514/256; 514/322; 514/326; 514/340; 514/397; 514/444; 540/472; 540/474

(58) Field of Search .............................. 514/79, 80, 89, 514/338, 340; 540/472, 474

(56) References Cited

U.S. PATENT DOCUMENTS

| 5,021,409 | A | 6/1991 | Murrer et al. ............... 514/183 |
| 5,583,131 | A | 12/1996 | Bridger et al. .............. 514/183 |
| 5,698,546 | A | 12/1997 | Bridger et al. .............. 514/183 |
| 5,817,807 | A | 10/1998 | Bridger et al. .............. 540/474 |

FOREIGN PATENT DOCUMENTS

| EP | 0 434385 A | 6/1991 |
| EP | 0 747 368 | 12/1996 |
| WO | WO92/16494 | 10/1992 |
| WO | WO93/12096 | 6/1993 |
| WO | WO95/18808 | 7/1995 |
| WO | WO 00/02870 A | 1/2000 |
| WO | WO 00/45814 A | 8/2000 |

OTHER PUBLICATIONS

International Search Repoert based on International Application No. PCT/CA99/00619.

Arenburg et al., "The Role CXC Chemokines in the Regulation of Angiogenesis in Non–small Cell Lung Cancer", J. Leukocyte Biol. 62(5):554–562 (1997).

Bleul et al., "The Lymphocyte Chemoattractant SDF–1 is a Ligand for LESTSR/Fusin and Blocks HIV–1 Entry", Nature, 382(6594): 829–832 (1996).

Boshoff et al., "Angiogenic and HIV–Inhibitory Functions of KSHV–Encoded Chemokines", Science, 278(5336):290–294 (1997).

Bridger et al., "Synthesis and Structure–Activity Relationships of Phenylenebis (methylene)–Linked Bis–Tetraazamacrocyles That Inhibit HIV Replication. Effects of Macrocyclic Ring Size and Substituents on the Aromatic Linker", J. Med. Chem. 38:366–378 (1995).

Bridger et al., "Synthesis and Structure–Activity Relationship of Phenylenebis (methylene)–Linked Bis–Tetraazamacrocyles That Inhibit HIV Replication. 2. Effect of Heteroaromatic Linkers on the Activity of Bicyclams", J. Med. Chem., 39(1):109–119 (1996).

Carroll et al. "Differential Regulation of HIV–1 Fusion Cofactor Expression by CD28 Costimulation of CD4$^+$ T Cells", Science, 276(5310):273–276 (1997).

Chemical Abstracts, 113:40649 (1990).

Chemical Abstracts, 111:190197 (1989).

Chemical Abstracts, 123:56538 (1994).

De Clercq et al., "Highly Potent and Selective Inhibition of Human Immunodeficiency Virus by the Byclam Derivative JM3100", Antimicrobial Agents & Chemotherapy, 38(4):668–674 (1994).

Donzella et al., "AMD3100, A Small Molecule Inhibitor of HIV–1 Entry Via the CXCR4 Co–Receptor", Nature Medicine, 4(1):72–77 (1998).

Fukuyama et al., "2– and 4–Nitrobenzenesulfonamides: Exceptionally Versatile Means for Preparation of Secondary Amines and Protection of Amines", Tetrahedron Letters, 36(36):6373–74 (1995).

Gupta et al., "Chemokine Receptors in Human Endothelial Cells", J. Biological Chem., 273(7):4282–87 (1998).

Hoxie et al., "CD4–Independent Infection by HIV–2 is Mediated by Fusin/CXCR4", Cell, 87:745–756 (1996).

Joao et al. "Quantitative Structural Activity Relationship Study of Bis–Tetraazacyclic Compounds. A Novel Series of HIV–1 and HIV–2 Inhibitors", J. Med. Chem. 38:3865–73 (1995).

(List continued on next page.)

Primary Examiner—Brenda Coleman
(74) Attorney, Agent, or Firm—Morrison & Foerster LLP

(57) ABSTRACT

The present invention is drawn to novel antiviral compounds, pharmaceutical compositions and their use. More specifically this invention is drawn to derivatives of monocyclic polyamines which have activity in standard tests against HIV-infected cells as well as other biological activity related to binding of ligands to chemokine receptors that mediate a number of mammalian embryonic developmental processes.

7 Claims, 3 Drawing Sheets

OTHER PUBLICATIONS

Leff, "Besides Aiding AIDS Entry, Receptor Honchos Fetal Growth of Brain, Gut, Blood Systems", Bioworld Today, 9:111 (1998).

Miedema et al., "Changing Virus–Host Interactions in the Course of HIV–1 Infection", Immunological Reviews, 140:35–72 (1994).

Morphy et al., "Towards Tumour Targeting with Copper–Radiolabelled Macrocycle–Antibody Conjugates: Synthesis, Antibody Linkage, and Complexation Behaviour", J. Chem. Soc. Perkin Trans., 2:573–85 (1990).

Oberlin et al., "The CXC Chemokine SDF–1 is the Ligand for LESTR/Fusin and Prevents Infection by T–Cell–Line–Adapted HIV–1", Nature, 382:833–835 (1996).

Ponath et al., "Chemokine Receptor Antagonists: Novel Therapeutics for Inflammaton and AIDS", Exp. Opin. Invest. Drugs, 7:1–18 (1998).

Schols et al., "Inhibition of T–Tropic HIV Strains by Selective Antagonization of the Chemokine Receptor CXCR4", Antiviral Research, 35:147–156 (1997).

Schols et al., "Bycyclams, A Class of Potent Anti–HIV Agents, are Targeted at the HIV Coreceptor Fusin/CXCR–4", Antiviral Research, 35:147–156 (1997).

Tachibana et al., "The Chemokine Receptor CXCR4 is Essential for Vascularization of the Goastrointestinal Tract", Nature, 393:591–94 (1998).

Wyatt et al., "The HIV–1 Envelope Glycoproteins: Fusogens, Antigens, and Immunogens", Science, 280:1884–88 (1998).

Zou et al., "Function of the Chemokine Receptor CXCR4 in Haematopoiesis and In Cerebellar Development", Nature, 393:595–99 (1998).

Example 1: AMD3465

Example 7: AMD3516

Example 2: AMD3538

Example 8: AMD3530

Example 3: AMD3500

Example 9: AMD3517

Example 4: AMD3499

Example 10: AMD3544

Example 5: AMD3498

Example 11: AMD3543

Example 6: AMD3497

Example 12: AMD3529

Example 13: AMD7049

Example 14: AMD7050

Example 15: AMD7051

Example 16: AMD7059

Example 17: AMD7063

Example 18: AMD7058

Example 19: AMD7032

Example 20: AMD7048

Example 21: AMD7060

Example 22: AMD7061

Example 23: AMD3451

Example 25: AMD3472

Example 24: AMD3454

Example 26: AMD3526

AMD3100

AMD3484

ANTIVIRAL COMPOUNDS

This is a continuation of U.S. Ser. No. 09/111,895 filed Jul. 8, 1998 U.S. Pat. No. 6,506,770 which is a continuation-in-part of U.S. application Ser. No. 08/659,500 filed Jun. 6, 1996, U.S. Pat. No. 5,817,807.

TECHNICAL FIELD OF THE INVENTION

The present invention is drawn to novel antiviral compounds, pharmaceutical compositions and their use. More specifically this invention is drawn to derivatives of monocyclic polyamines which have activity in standard tests against HIV-infected cells as well as other biological activity related to binding of ligands to chemokine receptors that mediate a number of mammalian embryonic developmental processes.

BACKGROUND OF THE INVENTION

Approximately 40 human chemokines have been described, that function, at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs*, 7:1–18, 1998). These chemotactic cytokines, or chemokines, constitute a family of proteins, approximately 8–10 kDa in size. Chemokines appear to share a common structural motif, that consists of 4 conserved cysteines involved in maintaining tertiary structure. There are two major subfamilies of chemokines: the "CC" or β-chemokines and the "CXC" or α-chemokines. The receptors of these chemokines are classified based upon the chemokine that constitutes the receptor's natural ligand. Receptors of the β-chemokines are designated "CCR"; while those of the a-chemokines are designated "CXCR".

Chemokines are considered to be principal mediators in the initiation and maintenance of inflammation. More specifically, chemokines have been found to play an important role in the regulation of endothelial cell function, including proliferation, migration and differentiation during angiogenesis and re-endothelialization after injury (Gupta et al., *J. Biolog. Chem.*, 7:4282–4287, 1998). Two specific chemokines have been implicated in the etiology of infection by human immunodeficiency virus (HIV).

In most instances, HIV initially binds via its gp120 envelope protein to the CD4 receptor of the target cell. A conformational change appears to take place in the gp120 which results in its subsequent binding to a chemokine receptor, such as CCR-5 (Wyatt et al., *Science*, 280:1884–1888 (1998)). HIV-1 isolates arising subsequently in the infection bind to the CXCR-4 chemokine receptor. In view of the fact that the feline immunodeficiency virus, another related retrovirus, binds to a chemokine receptor without needing to bind first to the CD4 receptor, suggests that chemokine receptors may be the primordial obligate receptors for immunodeficiency retroviruses.

Following the initial binding by HIV to CD4, virus-cell fusion results, which is mediated by members of the chemokine receptor family, with different members serving as fusion cofactors for macrophage-tropic (M-tropic) and T cell line-tropic (T-tropic) isolates of HIV-1 (Carroll et al., *Science*, 276: 273–276 1997). During the course of infection within a patient, it appears that a majority of HIV particles shift from the M-tropic to the more aggressive T-tropic viral phenotype (Miedema et al., *Immune. Rev.*, 140:35 (1994)) Curiously, the M-tropic viral phenotype correlates with the virus's ability to enter the cell following binding of the CCR-5 receptor, while the T-tropic viral phenotype correlates with viral entry into the cell following binding and membrane fusion with the CXCR-4 receptor. Clinically observations suggest that patients who possess genetic mutations in the CCR-5 or CXCR-4 appear resistant or less susceptible to HIV infection.

However, the binding of chemokine receptors to their natural ligands appears to serve a more evolutionary and central role than only as mediators of HIV infection. The chemokine receptor, CXCR-4 has been found to be essential for the vascularization of the gastrointestinal tract (Tachibana et al., *Nature*, 393:591–594 (1998)) as well as haematopoiesis and cerebellar development (Zou et al., *Nature*, 393:591–594 (1998)). Interference with any of these important functions served by the binding of pre-B-cell growth-stimulating factor/stromal derived factor (PBSF/SDF-1) to the CXCR-4 chemokine receptor results in lethal deficiencies in vascular development, haematopoiesis and cardiogenesis. Similarly, fetal cerebellar development appears to rely upon the effective functioning of CXCR-4 in neuronal cell migration and patterning in the central nervous system. This G-protein-coupled chemokine receptor appears to play a critical role in ensuring the necessary patterns of migration of granule cells in the cerebellar analog.

In attempting to better understand the relationship between chemokines and their receptors, recent experiments to block the binding of HIV to the CXCR-4 chemokine receptor were carried out through the use of monoclonal antibodies or small molecules that appear to suggest a useful therapeutic strategy (Schols et al., *J. Exp. Med.* 186:1383–1388 (1997); Schols et al., *Antiviral Research* 35:147–156 (1997)). Small molecules, such as bicyclams, appear to specifically interfere with the CXCR-4 binding and not CCR-5 binding (Donzella et al., *Nature Medicine*, 4:72–77 (1998)). These experiments demonstrated interference with HIV entry and membrane fusion into the target cell in vitro. Additional experiments monitoring the calcium flux or $Ca^{2+}$ mobilization assay demonstrated that a bicyclam also functioned as an antagonist to signal transduction resulting from the binding of stromal derived factor or SDF-1α, the natural chemokine to CXCR-4.

U.S. Pat. No. 5,583,131, U.S. Pat. No. 5,698,546 and allowed copending U.S. patent application Ser. No. 08/659, 500 disclose cyclic compounds that are active against HIV-1 an HIV-2 in in vitro tests. We have now discovered that these compounds exhibit anti-HIV activity due to their binding to the chemokine receptor 4 (CXCR-4 or Fusin receptor), expressed on the surface of certain cells of the immune system. This competitive binding thereby protects these target cells from infection by HIV which utilize the CXCR-4 receptor for entry. We have discovered that the disclosed compounds also antagonize the binding, signaling and chemotactic effects of the natural CXC-chemokine for CXCR-4, stromal cell-derived factor 1α (SDF-1α). Herein, we further disclose novel compounds that demonstrate protective effects against HIV infection of target cells by inhibition of binding in vitro to the CC-5 receptor (CCR-5).

SUMMARY OF THE INVENTION

The present invention provides novel compounds, that demonstrate protective effects on target cells from HIV infection as well as demonstrate other biological activities related to the ability of these compounds to inhibit the binding by the natural ligand to its chemokine receptor.

Accordingly, the present invention provides a macrocyclic compound of formula I:

$$V-CR^1R^2-Ar-CR^3R^4-N(R^5)-(CR^6R^7)_x-R^8 \quad (I)$$

wherein V is a cyclic polyamine moiety having a total of 9 to 24 members and from 3 to 6 optionally substituted amine nitrogens spaced by two or more optionally substituted carbon atoms from each other, and which may optionally comprise a fused aromatic or heteroaromatic ring;

$R^1$ to $R^7$ may be the same or different and are independently selected from hydrogen or straight, branched or cyclic $C_{1-6}$ alkyl;

$R^8$ is a heterocyclic group, a substituted aromatic group, or a mercaptan group;

Ar is an aromatic or heteroaromatic ring each optionally substituted at single or multiple positions with electrons-donating or withdrawing groups;

x is 1 or 2;

and the acid addition salts and metal complexes thereof.

Preferably V is a 14- to 17 membered fused or unfused ring system, such as a cyclam system or a 4,7,10,17-tetraazabicyclo[13.3.1]heptadeca-1(17),13,15-triene system or a derivative thereof, and especially a cyclam system or derivative thereof The moiety V may be substituted at C or N non-linking atoms, suitably by hydroxyl, alkoxy, thiol, thioalkyl or any other atom or group which does not adversely affect the activity or toxicity of the compounds but may reduce the basicity of the amines, for example halogen, nitro, carboxy, carboxyamido, sulphonic acid or phosphate. Suitably the fused aromatic or heteroaromatic ring is phenyl, pyridine, pyrimidine, pyrazine, imidazole or thiazole. Preferably, the fused aromatic or heteroaromatic ring is phenyl or pyridine.

Preferably $R^1$ to $R^7$ are each hydrogen.

Preferably $R^8$ is selected from pyridine, pyrimidine, pyrazine, imidazole, thiophene, thiophenyl, aminobenzyl, piperidinyl, piperazinyl or a mercaptan group.

Preferably Ar is phenyl. Preferred substituents are alkyl, aryl, amino, alkoxy, hydroxy, halogen, carboxyl and carboxamido.

The invention also includes what may be termed as "pro-drug", that is protected forms of the compounds, which release the compound after administration to a patient. For example, the compound may carry a protective groups which is split off by hydrolysis in body fluids e.g. in the bloodstream, thus releasing active compound or are oxidized or reduced in body fluids' to release the compound. A discussion or pro-drugs may be found in "Smith and Williams' Introduction to the Principles of Drug Design", H. J. Smith, Wright, Second Edition, London 1988.

Acid addition salts, for example hydrochlorides, and non-toxic labile metal complexes of compounds of formula I are also active compounds according to the present invention. Non-toxic in the present tense has to be considered with reference to the prognosis for the infected patient without treatment. Copper and zinc complexes are preferred although other metals such as nickel may be considered, whereas less labile metals such as cobalt and rhodium are less preferred because of likely lower selectivity.

Compounds of formula I are novel. Accordingly, a further aspect of the invention provides a process for the preparation of a compound of formula I which comprises the following steps:

(i) nucleophilic attack by the cyclic polyamine V having a single unprotected amine nitrogen, all other amine nitrogen atoms being protected, on an excess of a compound of formula II $$Y-CR^1R^2-Ar-CR^3R^4-Y \quad (II)$$

wherein $R^1$ to $R^4$ and Ar are as hereinbefore defined, and each Y is an active substituent which can be displaced by the unprotected nitrogen of polyamine V and is preferably selected from Br, Cl, I, methane sulphonate, 4-toluenesulphonate, trifluoromethane sulphonate.

It is well within the capabilities and knowledge of the skilled synthetic chemist to protect the amine nitrogens of cyclic polyamines, and it is preferred to use substitution by methanesulphonyl and/or toluenesulphonyl and/or diethoxyphosphoryl (see: Bridger et al, *J. Med. Chem.*, 38:366–378 (1995); Bridger et al, U.S. Pat. No. 5,583,131 or Bridger et al, U.S. Pat. No. 5,698,546) and/or nitrobenzenesulfonyl (Fukuyama et al., *Tetrahedron Letters* 1995, 36, 6373–6374.

The protected polyamine V is firstly reacted with a 5- to 10-fold excess of a compound of formula II in a solvent such as acetonitrile or dimethylformamide, tetrahydrofuran or dioxane and in the presence of a base, for example sodium carbonate or potassium carbonate. The reaction generally proceeds at room temperature to elevated temperature to give a cyclic polyamine in which all amine nitrogens are protected. In general, a mixture of products will be obtained and we have found that the product can conveniently be purified by silica gel chromatography or crystallization.

Nucleophilic attack of a compound of formula III $$R^5NH-(CR^6R^7)_x-R \quad (III)$$

wherein $R^5$ to $R^8$ and x are as hereinbefore defined on the product of the reaction described at (I) above, and subsequently de-protecting the amine nitrogens. The reaction with an excess of a compound of formula III is carried out under similar conditions to the reaction with the polyamine V.

The de-protection step is suitably carried out by re-fluxing the protected molecule in a mixture of aqueous HBr and acetic acid or concentrated sulphuric acid, or in the case of diethoxyphosphoryl in the presence of gaseous hydrogen chloride or gaseous hydrogen bromide in acetic acid; in the case of nitrobenzenesulfonyl deprotection, a mercaptan such as thiophenol or mercaptoacetic acid in the presence of a suitable base such as potassium carbonate, cesium carbonate, sodium hydroxide or lithium hydroxide in a solvent such as dimethylformamide, acetonitrile, tetrahydrofuran or dioxane is used. This reaction generally proceeds at room temperature to elevated temperatures to give a polyamine in which the nitrogens are deprotected. Alternatively, and accordingly, a further aspect of the invention provides a process for the preparation of compounds of Formula I which comprises the following steps:

(i) nucleophilic attack by the cyclic polyamine V having a single unprotected amine nitrogen, all other amine nitrogens being protected, with an excess of a compound of formula (IV)

$$Y-CR^1R^2-Ar-CR^3R^4-N(R^5)-(CR^6R^7)_x-R^8 \quad (IV)$$

Wherein $R^1$ to $R^4$ and x, $R^6$ to $R^8$ and Ar are as hereinbefore defined and Y is an active substituent which can be displaced by the unprotected nitrogen of cyclic polyamine V as hereinbefore defined. In this case, the intended substituent $R^5$ is hydrogen but for convenience, the nitrogen is protected as a nitrobenzenesulfonyl or diethoxyphosphoryl group.

The protected polyamine V is first reacted with a compound of formula IV using similar conditions to the reactions with compounds of formula II and formula III as described above and the product of this reaction is subjected to deprotection of the amine nitrogens on the polyamine and at $R^5$.

The deprotection steps were carried out as described above. For convenience, a sequential combination of these deprotection reactions may be used when both diethoxyphosphoryl and nitrobenzenesulfonyl groups are present.

The novel compounds further comprise a macrocyclic compound of general formula V:

$$V^2\text{—}CR^9R^{10}\text{—}Ar^2 \qquad (V)$$

where $V^2$ is a cyclic polyamine moiety having a total of 9 to 24 members and from 3 to 6 optionally substituted amine nitrogens spaced by two or more optionally substituted carbon atoms from each other, and which may optionally comprise a fused aromatic or heteroaromatic ring; where $R^9$ and $R^{10}$ may be the same or different and are independently selected from hydrogen or straight, branched or cyclic $C_{1-6}$ alkyl; further, where $Ar^2$ is an aromatic, fused aromatic, heterocyclic or fused heterocyclic ring each optionally substituted at single or multiple positions with electron-donating or withdrawing groups and/or aromatic and heterocyclic groups and their alkyl derivatives thereof; and the acid addition salts and metal complexes.

These novel compounds have demonstrated anti-HIV activity in an in vitro screen assay as presented in Table 1. These novel compounds have also demonstrated biological activity in inhibiting CXCR-4 specific monoclonal antibody (12G5) from binding to CXCR-4 on SUP-T1 cells by AMD compounds. These data are shown in Table 2 for AMD3100 (1,1'-[1,4-phenylenebis(methylene)]bis-1,4,8,11-tetraazacyclotetradecane tetrahydrochloride, AMD3465 (N-[1,4,8,11-tetraazacyclotetra-decanyl-1,4-phenylenebis (methylene)]-N-2-(aminomethyl)pyridine) and six new compounds: AMD 7049; AMD 7050; AMD 7051; AMD 7058; AMD 7059; and AMD 7063.

Data showing inhibition of the increased Ca2+ flux induced by SDF-1 in SUP-T1 cells (inhibition of signal transduction) by AMI compounds are shown in Table 3 for AMD3100, AMD3465 and compounds: AMD 7049; AMD 7050; AMD 7051; AMD 7058; AMD 7059; and AMD 7063.

Several novel compounds also inhibited infection of the cell line U87.CD4.CCR5 by the M-tropic HIV-1 strain BaL, which exclusively utilizes the CCR-5 co-receptor for entry. These data are shown in Table 4.

The experimental procedures for the mAb binding assay, the inhibition of $Ca^{2+}$ flux, and inhibition of infection by the HIV-1 BaL strain in U87.CD4.CCR5 cells would be readily understood by the skilled artisan. For example, see: Schols et al., *J. Exp. Med.* 186:1383–1388 (1997); Schols et al., *Antiviral Research* 35:147–156 (1997); and Donzella et al., *Nature Medicine*, 4:72–77 (1998). Also, the characterization of the CXCR-4 specific monoclonal antibody 12G5 is taught by Hoxie et al., *Cell,* 87:745–756 (1996).

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents.

Having now generally described the invention, the same will be more readily understood through reference to the following examples which are provided by way of illustration, and are not intended to be limiting of the present invention, unless specified.

As mentioned above, the compounds of the invention have activity against viral infections, especially retrovirus infections and specifically HIV. Accordingly, a further aspect of the invention provides a compound of formula I or formula V for use in medicine. More specifically, there is provided the use of a compound of formula I or formula V in the manufacture of a medicament for the treatment of HIV-infected patients. In the alternative, there is provided a method of treating an HIV-infected patient comprising administering to said patient, a pharmaceutically effective amount of a compound of formula I or formula V. Although compounds of formula I or formula V could be administered as the raw material, it is preferable to present them in the form of a pharmaceutical composition comprising a compound of formula I or formula V as active ingredient in admixture with a pharmaceutically acceptable diluent or carrier and optionally one or more other therapeutic ingredients, such compositions providing a further aspect of the invention.

In all aspects of the invention, it is understood that meso forms, enantiomers and resolved optically active forms of the compounds of formula I or formula V are also included. Also, it is to be considered within the invention, compounds of formula I or formula V diluted with non-toxic or other active substances.

BRIEF DESCRIPTION OF THE DRAWINGS

FIG. 1AA; shows the structural formula of compound AMD 3100.

FIG. 1AB; shows the structural formula of compound AMD 3484.

DETAILED DESCRIPTION OF THE INVENTION

Figure 1A:
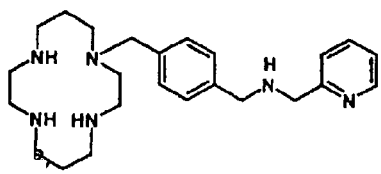
FIG. 1A, shows the structural formula of compound AMD 3465.
Figure 1G:
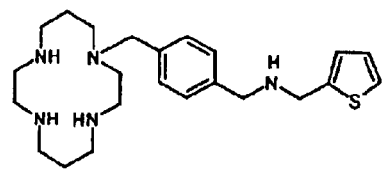
FIG. 1G; shows the structural formula of compound AMD 3516.
Figure 1B:
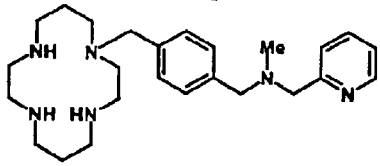
FIG. 1B, shows the structural formula of compound AMD 3538.
Figure 1H:
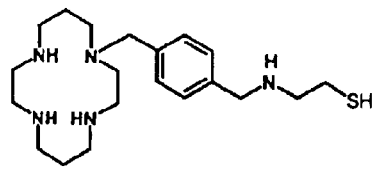
FIG. 1H; shows the structural formula of compound AMD 3530.
Figure 1C:
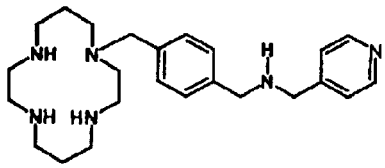
FIG. 1C; shows the structural formula of compound AMD 3500.
Figure 1I:
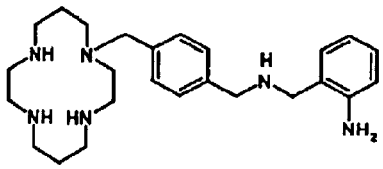
FIG. 1I; shows the structural formula of compound AMD 3517.
Figure 1D:
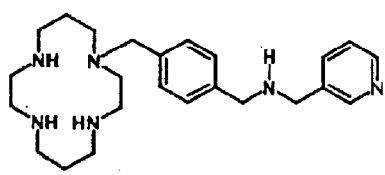
FIG. 1D; shows the structural formula of compound AMD 3499.
Figure 1J:
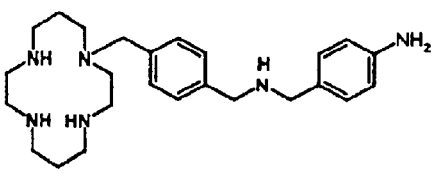
FIG. 1J; shows the structural formula of compound AMD 3544.
Figure 1E:
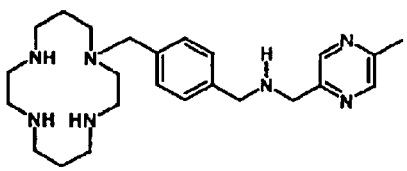
FIG. 1E; shows the structural formula of compound AMD 3498.
Figure 1K:
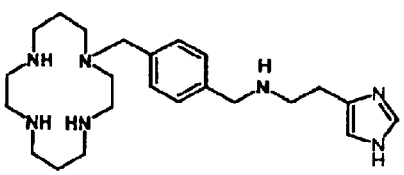
FIG. 1K; shows the structural formula of compound AMD 3543.
Figure 1F:
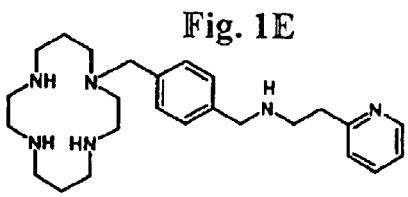
FIG. 1F; shows the structural formula of compound AMD 3497.
Figure 1L:
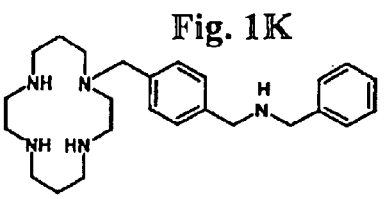
FIG. 1L; shows the structural formula of compound AMD 3529.
Figure 1M:
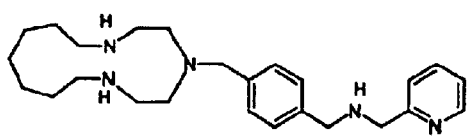
FIG. 1M; shows the structural formula of compound AMD 7049.
Figure 1N:
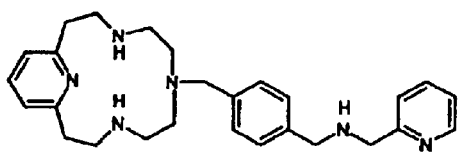
FIG. 1N; shows the structural formula of compound AMD 7050.
Figure 1O:
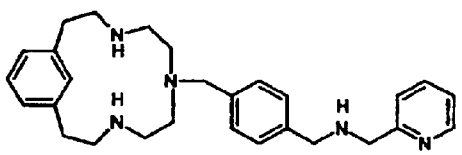
FIG. 1O; shows the structural formula of compound AMD 7051.
Figure 1P:
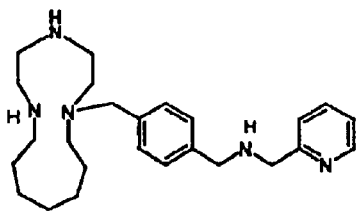
FIG. 1P; shows the structural formula of compound AMD 7059.
Figure 1Q:
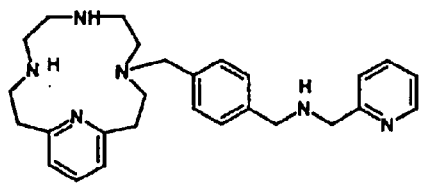
FIG. 1Q; shows the structural formula of compound AMD 7063.
Figure 1R:
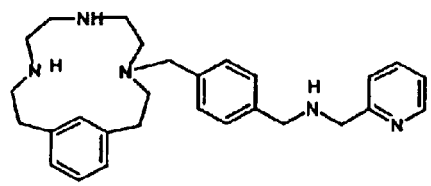
FIG. 1R; shows the structural formula of compound AMD 7053.
Figure 1S:
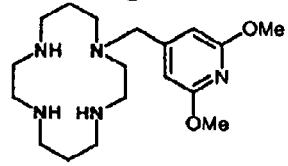
FIG. 1S; shows the structural formula of compound AMD 7032.
Figure 1T:
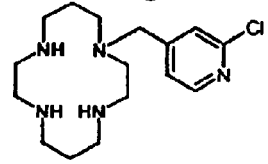
FIG. 1T; shows the structural formula of compound AMD 7060.
Figure 1U:
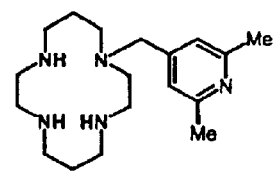
FIG. 1U; shows the structural formula of compound AMD 7061.
Figure 1V:
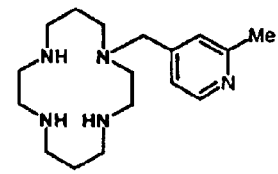
FIG. 1V; shows the structural formula of compound AMD 7061.
Figure 1W:
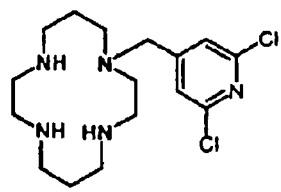
FIG. 1W; shows the structural formula of compound AMD 3451.
Figure 1Y:
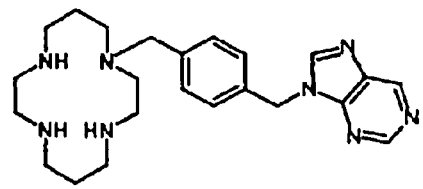
FIG. 1Y; shows the structural formula of compound AMD 3452.
Figure 1X:
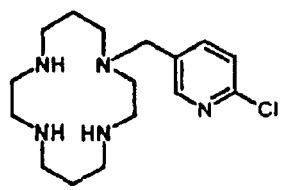
FIG. 1X; shows the structural formula of compound AMD 3457.
Figure 1Z:
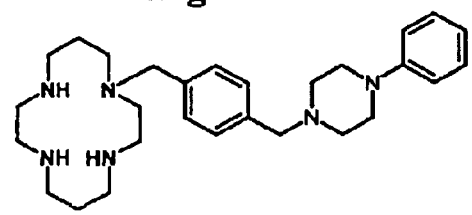
FIG. 1Z; shows the structural formula of compound AMD 3726.
Figure 1A:
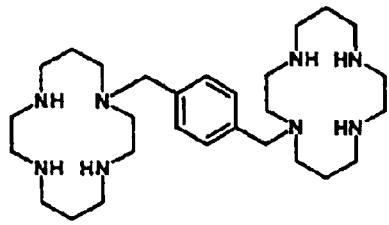
Figure 1A:
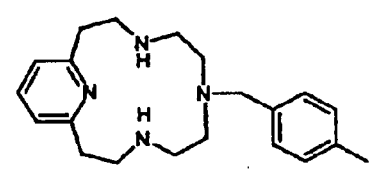

Terms as used herein are based upon their art recognized meaning unless otherwise indicated and should be clearly understood by the ordinary skilled artisan. The present invention will now be illustrated by the following preparative Examples.

General Procedure A

1-[1-Methylene-4-(bromomethylene)phenylene]-4,8,11-tris(diethoxyphosphoryl)-1,4,8,11-tetraazacyclotetradecane To a stirred solution of 4,8,11-Tris(diethoxyphosphoryl)-1,4,8,11-tetraazayclotetradecane (See Bridger et al. *J Med. Chem.* 1995, 38, 366–378) (6.1 g, 0.01 mol) and $K_2CO_3$ (1.89 g, 0.013 mol) in $CH_3CN$ (150 ml) was added α,α'-dibromo-p-xylene (13.2 g, 0.05 mol) and the reaction mixture stirred at 70° C. for 1 hour. The solution was cooled to room temperature and the solvent removed under reduced pressure. The residue was partitioned between brine (50 ml) and $CH_2Cl_2$ (100 ml). The organic phase was separated, dried ($Na_2SO_4$) and concentrated to a minimum volume. The solid was filtered off and the solvent evaporated under reduced pressure to give the crude product as a pale yellow oil. Purification by column chromatography in silica gel ($CH_2Cl_2\backslash CH_3OH$, 25:1) gave 1-[1-methylene-4-(bromomethylene)phenylene]-4,8,11-tris(diethoxyphosphoryl-1,4,8,11-tetraazacyclotetradecane (4.7 g, 59%) as a pale yellow oil. $^1H$ NMR ($CDCl_3$) δ 1.21–1.37 (m, 18H), 1.66–1.74 (m, 2H), 1.82–1.91 (m, 2H), 2.30–2.35 (m, 2H), 2.58–2.63 (m, 2H), 2.99–3.16 (m, 12H), 3.48 (s, 2H), 3.95–4.07 (m, 12H), 4.48 (s, 2H), 7.21–7.35 (4H).

General Procedure B

Second Alkylation of the Bromobenzyl Cyclam Intermediate with an Amine (See for Example: Bridger et al. *J. Med. Chem.* 1995, 38, 366–378)

To a solution of the appropriate amine (5.0 equiv.) in dry $CH_3CN$ (5 mL) containing a suspension of $K_2CO_3$ (1.5 equiv.) at 80° C. was added dropwise with stirring a solution of 1-[1-methylene-4-(bromomethylene)phenylene]-4,8,11-tris(diethoxyphosphoryl-1,4,8,11-tetraazacyclotetradecane (0.6 mmol) in $CH_3CN$ (10 ml) over 15–20 min. After stirring for a further 1 hour at 80° C. the solution was concentrated to dryness and the residue was partitioned between $CH_2Cl_2$ and water. The organic layer was separated and washed with water (3×) then dried ($MgSO_4$) and evaporated. The crude residue was purified by column chromatography on silica gel eluting with 5–15% $MeOH/CH_2Cl_2$ to afford a viscous oil.

General Procedure C

De-protection of the Diethoxyphosphoramidate Groups Using HBr/HOAc at Room Temperature (See for Example: Bridger et al. *J. Med. Chem.* 1995, 38, 366–378)

To a stirred solution of the protected cyclam derivative from procedure B (0.1–0.5 mmol) in acetic acid (3 mL) was added 30% HBr in acetic acid (Aldrich, 5 mL) and the solution was stirred at room temperature for 14 hours. The resulting precipitate was collected by filtration and washed with acetic acid then $Et_2O$. The solid was then dissolved in $H_2O$ (3 mL) and treated with charcoal (100 mg) and the mixture was heated to 80° C. for 30 min. The hot solution was filtered through celite and the filtrate was concentrated to approximately 1 mL after which acetic acid was added resulting in the immediate formation of a white precipitate. The white solid was collected by filtration and dried in vacuo.

The following compounds were prepared by these methods:

EXAMPLE 1

N-[1,4,8,11-Tetraazacyclotetradecanyl-1,4-phenylenebis(methylene)]-2-(amino-methyl)pyridine hexahydrobromide (AMD 3465)

White solid: Mp 200–205° C. (dec); $^1H$ NMR ($D_2O$) δ 2.04 (m, 4H), 3.20–3.40 (m, 8H), 3.40–3.60 (m, 8H), 4.34 (s, 2H), 4.38 (s, 2H), 4.51 (s, 2H), 7.50 (m, 4H), 7.75 (t, 1H, J=6.6 Hz), 7.82 (d, 1H, J=7.9 Hz), 8.26 (t, 1H, J=7.9 Hz), 8.63 (d, 1H, J=5.3 Hz); $^{13}C$ NMR ($D_2O$) δ 18.30, 18.96, 37.04, 37.28, 37.40, 40.92, 41.13, 41.49, 44.26, 47.61, 48.01, 51.29, 58.88, 127.46, 127.75, 130.40; 131.05, 131.23, 131.47, 132.10, 132.44, 144.95, 145.81, 146.01; FAB MS m/z 493 (M+$H^{81}Br$, 7), 491 (M+$H^{79}Br$, 7), 411 (M+H, 100).

Anal. ($C_{24}H_{38}N_6$·6HBr); Calc. C, 32.36; H, 4.98; N, 9.44; Br, 53.21. Found C, 32.20; H, 5.00; N, 9.30; Br, 53.10.

EXAMPLE 2

N-[1,4,8,11-Tetraazacyclotetradecanyl-1,4-phenylenebis(methylene)]-N-methyl-2-(aminomethyl)pyridine hexahydrobromide hydrate (AMD 3538)

White solid: Mp 220–225° C. (dec); $^1H$ NMR ($D_2O$) δ 2.06 (m, 4H), 2.76 (s, 3H), 3.20–3.65 (m, 16H), 4.47 (bs, 4H), 4.65 (s, 2H), 7.54 (bs, 4H), 7.80 (t, 1H), 7.87 (d, 1H), 8.28 (t, 1H), 8.68 (d, 1H); $^{13}C$ NMR ($D_2O$) δ 18.14, 18.75, 18.89, 36.74, 37.04, 37.15, 37.62, 40.38, 40.72, 40.91, 41.28, 44.05, 47.50, 56.98, 58.88, 60.28, 127.60, 128.86, 130.78, 130.96, 132.16, 132.64, 144.91, 145.04, 146.12; FAB MS m/z 507 (M+$H^{81}Br$, 27), 507 (M+$H^{79}Br$, 22), 425 (M+H, 100).

Anal. ($C_{25}H_{40}N_6$·6HBr·1.5$H_2O$); Calc. C, 32.04; H, 5.27; N, 8.97; Br, 51.1,6. Found C, 31.88; H, 5.30; N, 8.93; Br, 51.00.

EXAMPLE 3

N-[1,4,8,11-Tetraazacyclotetradecanyl-1,4-phenylenebis(methylene)]-4-)amino-methyl)pyridine hexahydrobromide (AMD 3500)

White solid: mp 201–204° C. (dec); $^1H$ NMR ($D_2O$) δ 1.91–2.12 (m, 4H), 3.00–3.49 (m, 16H), 4.13 (s, 2H), 4.34

(s, 2H), 4.53 (s, 2H), 7.39–7.57 (m, 4H), 8.02 (d, 2H, J=6.3 Hz), 8.74 (d, 2H, J=6.3 Hz); $^{13}$C NMR (D$_2$O) δ 18.26, 18.88, 36.94, 37.29, 37.36, 40.89, 41.06, 41.44, 44.21, 47.61, 49.17, 51.43, 59.02, 127.84, 130.21, 131.64, 132.15, 132.45, 142.19, 151.67; FAB MS m/z 493 (M+H$^{81}$Br, 8), 491 (M+H$^{79}$Br, 10), 411 (M+H, 83), 320 (37), 247 (58), 201 (100).

Anal. (C$_{24}$H$_{38}$N$_6$.6HBr); Calc. C, 32.17; H, 4.95; N, 9.34; Br, 53.50. Found C, 32.16; H, 5.03; N, 9.41; Br, 53.28.

EXAMPLE 4

N-[1,4,8,11-Tetraazacyclotetradecanyl-1,4-phenylenebis(methylene)]-3-(amino-methyl)pyridine hexahydrobromide (AMD 3499)

White solid: mp 198–202° C. (dec); $^1$H NMR (D$_2$O) δ 1.83–2.07 (m, 4H), 2.96–3.47 (m, 16H), 4.11 (s, 2H), 4.32 (s, 2H), 4.49 (s, 2H), 7.38–7.56 (m, 4H), 8.04 (t, 1H, J=6.4 Hz), 8.63 (d, 1H, J=8.3 Hz), 8.76 (d, 1H, J=5.6 Hz), 8.86 (s, 1H); $^{13}$C NMR (D$_2$O) δ 18.23, 18.87, 36.92, 37.29 (2C), 40.88, 41.05, 41.43, 44.17, 47.22, 47.60, 51.18, 59.04, 128.29, 130.01, 131.49, 132.14, 132.66 (2C), 142.55, 142.76, 148.98; FAB MS m/z 493 (M+H$^{81}$Br, 7), 491 (M+H$^{79}$Br, 6), 411 (M+H, 100), 320 (33), 247 (24).

Anal. (C$_{24}$H$_{38}$N$_6$.6HBr); Calc. C, 32.17; H, 4.95; N, 9.34; Br, 53.50. Found C, 32.08; H, 5.02; N, 9.25; Br, 53.28.

EXAMPLE 5

N-[1,4,8,11-Tetraazacyclotetradecanyl-1,4-phenylenebis(methylene)]-(2-amino-methyl-5-methyl)pyrazine pentahydrobromide (AMD 3498)

White solid: mp 194–197° C. (dec); $^1$H NMR (D$_2$O) δ 1.93–2.12 (m, 4H), 2.42 (s, 3H), 3.25 (s, 8H), 3.48 (s, 8H), 4.28 (s, 2H), 4.30 (s, 2H), 4.33 (s, 2H), 7.44 (s, 4H), 8.33 (s, 1H), 8.46 (s, 1H); $^{13}$C NMR (D$_2$O) δ 18.01, 18.72, 19.80, 36.66, 37.05, 37.13, 40.70, 40.89, 41.27, 43.99, 47.47, 48.14, 50.61, 59.06, 129.97, 131.43, 132.04, 132.99, 140.93, 144.98, 146.49, 153.51; FAB MS m/z 509 (M+H$^{81}$Br, 17), 507 (M+H$^{79}$Br, 15), 426 (M+H, 100), 320 (21), 247 (20).

Anal. (C$_{24}$H$_{39}$N$_7$.5.5HBr); Calc. C, 33.10; H, 5.15; N, 11.26; Br, 50.47. Found C, 32.80; H, 5.41; N, 11.00; Br, 50.58.

EXAMPLE 6

N-[1,4,8,11-Tetraazacyclotetradecanyl-1,4-phenylenebis(methylene)]-2-(amino-ethyl)pyridine hexahydrobromide (AMD 3497)

White solid: mp 195–198° C. (dec); $^1$H NMR (D$_2$O) δ 1.98–2.17 (m, 4H), 3.20–3.38 (m, 8H), 3.38–3.63 (m, 12H), 4.27 (s, 2H), 4.39 (s, 2H), 7.50 (s, 4H), 7.80–7.89 (m, 2H), 8.42 (m, 1H), 8.58 (d, 1H, J=5.8 Hz); $^{13}$C NMR (D$_2$O) δ 18.51, 19.14, 29.85, 37.56 (3C), 41.21, 41.41, 41.82, 44.57, 45.27, 47.83, 51.10, 58.74, 126.35, 127.93, 130.66, 131.27, 131.99, 132.69, 141.89, 147.79, 150.91; FAB MS m/z 507 (M+H$^{81}$Br, 40), 505 (M+H$^{79}$Br, 34), 425 (M+H, 100).

Anal. (C$_{25}$H$_4$OH$_6$.6HBr); Calc. C, 32.99; H, 5.09; N, 9.23; Br, 52.67. Found C, 32.79; H, 5.34; N, 9.11; Br, 52.45.

EXAMPLE 7

N-[1,4,8,11-Tetraazacyclotetradecanyl-1,4-phenylenebis(methylene)]-2-(amino-methyl) thiophene pentahydrobromide (AMD 3516)

White solid: mp 245–248° C. (dec); $^1$H NMR (D$_2$O) δ 1.87–2.12 (m, 4H), 3.02–3.51 (m, 16H), 4.17 (s, 4H), 4.38 (s, 2H), 6.97 (t, 1H, J=3.9 Hz), 7.13 (d, 1H, J=3.1 Hz), 7.41 (s, 5H); $^{13}$C NMR (D$_2$O) δ 18.80, 19.52, 38.03, (3C), 41.59 (2C), 42.21, 44.89 (2C), 48.15, 49.83, 58.52, 128.13, 129.12, 131.15, 131.47, 131.50, 131.90, 132.42, 132.87; FAB MS m/z 498 (M+H$^{81}$Br, 11), 496 (M+H$^{79}$Br, 9), 416 (M+H, 53), 218 (100), 201 (64).

Anal. (C$_{23}$H$_{37}$N$_5$S.5HBr); Calc. C, 33.68; H, 5.16; N, 8.54; Br, 48.71. Found C, 33.85; H, 5.22; N, 8.50; Br, 48.52.

EXAMPLE 8

N-[1,4,8,11-Tetraazacyclotetradecanyl-1,4-phenylenebis(methylene)]-2-(amino-ethyl)mercaptan pentahydrobromide dihydrate (AMD 3530)

White solid: mp 234–236° C. (dec); $^1$H NMR (D$_2$O) δ 1.75–2.05 (m, 4H), 2.75–3.45 (m, 20H), 4.05 (s, 2H), 4.15 (s, 2H), 7.35 (s, 4H); FAB MS m/z 462 (MH+HS$^{81}$Br, 15), 460 (MH+H$^{79}$Br, 15), 380 (M+H, 100), 300 (64), 279 (47), 239 (49).

Anal. (C$_{20}$H$_{37}$N$_5$.S.5HBr)2H$_2$O.0.5HOAc) requires C, 29.67; H, 5.69; N, 8.24; Br, 46.99. Found C, 29.31; H, 5.72; N, 8.25; Br, 46.64.

EXAMPLE 9

N-[1,4,8,11-Tetraazacyclotetradecanyl-1,4-phenylenebis(methylene)]-2-amino-benzylamine pentahydrobromide (AMD 3517)

White solid: mp 203–206° C. (dec); $^1$H NMR (D$_2$O) δ 1.85–2.13 (m, 4H), 3.02–3.58 (m, 16H), 4.23 (s, 2H), 4.31 (s, 4H), 7.23–7.54 (m, 8H); $^{13}$C NMR (D$_2$O) δ 18.03, 19.29, 37.78 (3C), 41.37 (2C), 42.00, 44.82, 46.25, 47.96, 51.16, 58.68, 124.04, 124.40, 129.40, 130.75, 131.21 (2C), 131.88, 131.96, 132.46, 132.83; FAB MS m/z 507 (M+H$^{81}$Br, 15), 505 (M+H$^{79}$Br, 18), 425 (M+H, 100), 320 (30), 201 (51).

Anal. (C$_{25}$H$_{40}$N$_6$.5.75HBr.0.5H$_2$O). Calc. C, 33.42; H, 5.19; N, 9.35; Br, 51.14. Found C, 33.69; H, 5.35; N, 9.00; Br, 51.13.

EXAMPLE 10

N-[1,4,8,11-Tetraazacyclotetradecanyl-1,4-phenylenebis(methylene)]-4-amino-benzylamine hexahydrobromide (AMD 3544)

Yellow solid: mp 120–125° C. (dec); $^1$H NMR (D$_2$O) δ 1.8–2.0 (m, 4H), 2.9–3.4 (m, 16H), 4.1 (s, 2H), 4.18 (s, 4H), 7.2–7.5 (m, 8H); $^{13}$C NMR (D$_2$O) δ 18.86, 19.57, 38.14, 41.76, 43.74, 45.14, 48.24, 50.14, 50.42, 51.49, 58.38, 124.13, 131.13, 131.30, 131.83, 131.92, 131.96, 132.67; FAB MS m/z 507 (M+H$^{81}$Br, 5), 505 (M+H$^{79}$Br, 5), 425 (M+H, 45), 201 (47), 155 (75), 106 (100).

Anal. (C$_{25}$H$_{40}$N$_6$.6HBr.HOAc) requires C, 33.43; H, 5.19; N, 8.66; Br, 49.42; O, 3.30. Found C, 33.42; H, 5.49; N, 8.62; Br, 49.23.

EXAMPLE 11

N-[1,4,8,11-Tetraazacyclotetradecanyl-1,4-phenylenebis(methylene)]-4-(amino-ethyl)imidazole hexahydrobromide (AMD 3543)

Off white solid: mp 135–140° C. (dec); $^1$H NMR (D$_2$O) δ 1.75 (m, 2H), 190 (m, 2H), 2.70–3.27 (m, 20H), 3.77 (s, 2H), 4.14 (s, 2H), 7.18 (s, 1H), 7.25 (d, 2H, J=7.97 Hz), 7.37 (d, 2H, J=7.97 Hz), 8.48 (s, 1H); FAB MS m/z 496 (M+H$^{81}$Br, 5), 494 (M+H$^{79}$Br, 5), 414 (M+H, 17), 201 (15).

Anal. ($C_{23}H_{39}N_7 \cdot 6HBr$) requires C, 30.73; H, 5.04; N, 10.91; Br, 53.32. Found C, 30.39; H, 5.41; N, 10.41; Br, 53.66.

EXAMPLE 12

N-[1,4,8,11-Tetraazacyclotetradecanyl-1,4-phenylenebis(methylene)]-benzylamine pentahydrobromide (AMD 3529)

Off white solid: mp 245–250° C. (dec); $^1$H NMR ($D_2O$) δ 1.9–2.1 (m, 4H), 3.2–3.6 (m, 16H), 4.12 (s, 2H), 4.15 (s, 2H), 4.36 (s, 2H), 7.30 (s, 5H), 7.41 (d, 2H, J=8.3 Hz) 7.46 (d, 2H, J=8.3 Hz); $^{13}$C NMR($D_2O$) δ 18.43, 19.06, 37.29, 37.46, 37.63, 41.09, 41.32, 41.68, 44.46, 47.74, 50.18, 51.00, 58.79, 129.53, 129.97, 130.18, 130.35, 130.68, 131.18, 131.92, 133.14; FAB MS m/z 492 (M+H$^{81}$Br, 13), 490 (M+H$^{79}$Br, 13), 410 (M+H, 100), 201 (36).

Anal. ($C_{25}H_{39}N_5 \cdot 5HBr$); requires C, 36.88; H, 5.45; N, 8.60; Br, 49.07. Found C, 36.79; H, 5.56; N, 8.48; Br, 48.79.

The compounds of the invention were tested in a screen by the MTT method (*J. Virol. Methods* 120:309–321 (1988)). MT-4 cells ($2.5 \times 10^4$/well) were challenged with HIV-1 (HTLV-IIIB) or HIV-2 (LAV-2 ROD) at a concentration of 100 CCID$_{50}$ and incubated in the presence of various concentrations of the test compounds, which were added immediately after challenge with the virus. After 5 days culture at 37° C. in a $CO_2$ incubator, the number of viable cells was assessed by the MTT (tetrazolium) method. Antiviral activity and cytotoxicity of the compounds are expressed in Table 1 below as EC$_{50}$ (μg/ml) and CC$_{50}$ (μg/ml), respectively. The potential therapeutic usefulness was assessed by calculating a Selectivity Index (SI) corresponding to the ratio of CC$_{50}$ to EC$_{50}$.

TABLE 1

Anti-HIV activity data

| Compound | CC$_{50}$ (μg/mL) | EC$_{50}$ (μg/mL) HIV-1 (IIIB) | EC$_{50}$ (μg/mL) HIV-2 | SI HIV-1 |
|---|---|---|---|---|
| 1 AMD3465 | >250 | 0.008 | 0.032 | $3 \times 10^4$ |
| 2 AMD3538 | 209 | 0.1 | 6.7 | $2.0 \times 10^3$ |
| 3 AMD3500 | >250 | 0.6 | 10.3 | 417 |
| 4 AMD3499 | >250 | 1.8 | 28.5 | 138 |
| 5 AMD3498 | >250 | 0.2 | 7.1 | $1.2 \times 10^3$ |
| 6 AMD3497 | >250 | 1.8 | 3.8 | 138 |
| 7 AMD3516 | 158 | 0.7 | 9.8 | 225 |
| 8 AMD3530 | 175 | 0.5 | 2.0 | 350 |
| 9 AMD3517 | 153 | 0.8 | 10.6 | 191 |
| 10 AMD3544 | 222 | 0.7 | 3.7 | 317 |
| 11 AMD3543 | 239 | 0.2 | 1.0 | $1 \times 10^3$ |
| 12 AMD3529 | 130 | 0.4 | 2.6 | 325 |

In this field of study, it is considered that any compound exhibiting a Selectivity Index of greater than 100 has the considerable potential for further study. HIV is one of the most challenging viruses to combat, and the results given above provide an indication of activity against other retroviruses and against other viruses in general.

EXAMPLE 13

N-[4-(1,4,7-Triazacyclotetra-Decanyl)-1,4-phenylenebis(methylene)]-2-(aminomethyl)pyridine (AMD 7049)

N,N'-Bis(2-Nitrobenzenesulfonyl)-1,7-heptanediamine

To a stirred solution of 1,7-heptanediamine (5.01 g, 38.5 mmol) and Et$_3$N (13.5 mL, 96.9 mmol) in $CH_2Cl_2$ (70 mL) was added a solution of 2-nitrobenzenesulfonyl chloride (18.80 g, 84.83 mmol) in $CH_2Cl_2$ (40 mL). The mixture was stirred at room temperature under nitrogen for 72 h and then concentrated in vacuo. The residue was stirred in diethyl ether (100 mL), and the precipitate was collected by filtration and washed with $H_2O$ (300 mL) followed by diethyl ether (300 mL) to give a gray solid (18.5 g, 96%): $^1$H NMR (DMF-d$_7$) δ 1.21 (m, 6H), 1.49 (m, 4H), 3.04 (m, 4H), 7.87 (m, 2H), 7.95 (m, 4H), 8.04 (m, 2H), 8.15 (m, 2H).

General Procedure D

4-Diethoxyphosphoryl-1,7-bis(2-nitrobenzenesulfonyl)-1,4,7-triazacyclotetradecane To a stirred solution of N,N'-bis(2-nitrobenzenesulfonyl)-1,7-heptanediamine (9.00 g, 18.0 mmol) and $Cs_2CO_3$ (17.8 g, 54.6 mmol) in DMF (500 mL) under nitrogen maintained at 80° C. was added dropwise a solution of N-(diethoxyphosphoryl)-O,O'-bis(2-methylsulfonyl)diethanolamine (Bridger et al., J. Med. Chem. 1995, 38, 366–378) (7.95 g, 20.0 mmol) in DMF (50 mL) over 8 h. Heating was continued for a further 17 h and the mixture was then allowed to cool and concentrated in vacuo. The residue was partitioned between CHCl$_3$ (140 mL) and $H_2O$ (80 mL) and the aqueous layer was separated and extracted with CHCl$_3$ (3×40 mL). The combined organic extracts were dried (MgSO$_4$) and concentrated in vacuo and the residue was purified by column chromatography on silica gel (ethylacetate) to give the desired macrocycle as a yellow crystalline solid (2.85 g, contaminated with DMF).

To remove the unwanted DMF impurity, the residue was dissolved in EtOAc (75 mL), and the solution was washed sequentially with 5% NaHCO$_3$ (2×10 mL) and brine (5×10 mL), dried (MgSO$_4$) and evaporated to give a yellow amorphous solid (2.52 g, 20%): $^1$H NMR (CDCl$_3$) δ 1.32 (t, 6H, J=7.1 Hz), 1.51 (m, 6H), 1.61 (m, 4H), 3.33 (m, 12H), 4.03 (m, 4H), 7.61 (m, 2H), 7.71 (m, 4H), 8.03 (m, 2H).

General Procedure E

Synthesis of 1,7-Bis(2-nitrobenzenesulfonyl)-1,4,7-triazacyclotetradecane

To a stirred suspension of the macrocycle from above (1.88 g, 2.66 mmol) in acetic acid (5 mL) was added a freshly prepared solution of saturated HBr(g) in acetic acid (20 mL) and the resulting homogeneous solution was stirred at room temperature for a further 22 h. Addition of diethyl ether (250 mL) to the reaction mixture gave a precipitate that was allowed to settle to the bottom of the flask and the supernatant solution was decanted. The precipitate was washed with ether by decantation (repeated 3×) and the residue was then partitioned between $CH_2Cl_2$ (40 mL) and 1N aqueous NaOH (25 mL). The separated aqueous layer was extracted with $CH_2Cl_2$ (2×20 mL) and the combined organic extracts were washed with brine (20 mL), then dried (MgSO$_4$) and concentrated in vacuo to give a yellow amorphous solid (1.23 g, 81%): $^1$H NMR (CDCl$_3$) δ 1.46–1.67 (m, 10H), 2.90 (m, 4H), 3.34 (m, 8H), 7.61 (m, 2H), 7.70 (m, 4H), 7.97 (m, 2H).

4-Bromomethylbenzyl Alcohol

To a solution of methyl 4-bromomethylbenzoate (5.73 g, 25 mmol) in dry $CH_2Cl_2$ (150 mL) cooled to −78° C. with stirring under nitrogen was added dropwise a solution of DIBAL-H (82.5 mL, 1.0 M solution in THF). Stirring was continued for 1.5 h at −78° C., and the reaction mixture was then allowed to warm to 0° C. and quenched with $H_2O$. The organic layer was separated and the aqueous was extracted with $CH_2Cl_2$ (2×100 mL). The combined organic extracts were dried ($MgSO_4$) and evaporated to give the desired alcohol (5.0 g, 100%) as a white solid: $^1H$ NMR ($CDCl_3$) δ 1.84 (br, 1H), 4.49 (s, 2H), 4.67 (s, 2H), 7.33 (d, 2H, J=8.2 Hz), 7.38 (d, 2H, J=8.2 Hz).

N-(2-Nitrobenzenesulfonyl)-2-(aminomethyl)pyridine

A solution of 2-nitrobenzenesulfonylchloride (16.62 g, 0.075 mol) in dry $CH_2Cl_2$ (120 mL) was added dropwise via cannula to a stirred solution of 2-(aminomethyl)pyridine (5.41 g, 0.05 mol) and $Et_3N$ (13.9 mL, 0.10 mol) in dry $CH_2Cl_2$ (150 mL) under nitrogen. The reaction mixture was stirred for three hours at room temperature, and then quenched with water (20 mL). The aqueous layer was separated and extracted with EtOAc (5×80 mL). The combined organic extracts were dried ($MgSO_4$) and evaporated to small volume to give a white precipitate which was collected by filtration and washed with cold $CH_2Cl_2$ to give the desired product (11.37 g, 78%) as a white solid: $^1H$ NMR (Acetone-$d_6$) δ 4.46 (s, 2H), 7.19 (d, 1H, J=7.4, 4.5 Hz), 7.25–7.35 (br s, 1H), 7.39 (d, 1H, J=7.7 Hz), 7.68 (ddd, 1H, J=7.7, 7.5, 1.8 Hz), 7.76–7.88 (m, 2H), 7.94 (dd, 1H, J=7.7, 1.5 Hz), 8.04 (dd, 1H, J=7.5,1.8 Hz), 8.38 (d, 1H, J=4.5 Hz).

N-[1-Methylene-4-(hydroxymethylene)phenylene]-N-(2-Nitrobenzenesulfonyl)-2-(aminomethyl)pyridine A mixture of N-(2-nitrobenzenesulfonyl)-2-(aminomethyl)pyridine (5.87 g, 20 mmol), 4-bromomethylbenzyl alcohol (4.02 g, 20 mmol) and $K_2CO_3$ (5.53 g, 40 mmol) in dry $CH_3CN$ (150 mL) were heated at 60° C. for 4 h with stirring under nitrogen. The mixture was then allowed to cool to room temperature, the solvent evaporated and the residue was partitioned between water and $CH_2Cl_2$. The separated aqueous phase was extracted with $CH_2Cl_2$, and the combined organic extracts were dried ($MgSO_4$) and evaporated. The residue was suspended in ethyl acetate/hexane (1:1) and collected by filtration to give the desired product (6.87 g, 83%) as a white solid: $^1H$ NMR ($CDCl_3$) δ 1.78 (t, 1H, J=5.8 Hz), 4.58 (s, 2H) 4.60 (s, 2H), 4.64 (d, 2H, J=5.8 Hz), 7.13–7.26 (m, 6H), 7.54–7.59 (m, 2H), 7.66–7.68 (m, 2H), 7.98 (d, 1H, J=7.4 Hz), 8.40 (d, 1H, J=3.8 Hz).

N-[1-Methylene-4-(chloromethylene)phenylene]-N-(2-nitrobenzenesulfonyl)-2-(aminomethyl)pyridine To a stirred solution of the alcohol from above (1.91 g, 4.62 mmol) and $Et_3N$ (2.0 mL, 14 mmol) in $CH_2Cl_2$ (20 mL) cooled in an ice bath under nitrogen, was added methanesulfonyl chloride (0.73 mL, 9.4 mmol) and the reaction mixture was then heated to reflux for a further 6 h. The solution was diluted with $CH_2Cl_2$ (60 mL) and washed with 10% aqueous HCl (2×20 mL), 5% aqueous $NaHCO_3$ (20 mL), and $H_2O$ (25 mL) then dried ($MgSO_4$) and concentrated in vacuo to give an orange oil (1.95 g, 98%): $^1H$ NMR ($CDCl_3$) δ 4.52 (s, 2H), 4.60 (s, 4H), 7.12–7.26 (m, 6H), 7.55 (m, 2H), 7.67 (d, 2H, J=4.0 Hz), 7.94 (d, 1H, J=8.0 Hz), 8.41 (d, 1H, J=4.8 Hz). This was used without further purification.

General Procedure F

N-[4-[1,7-Bis(2-nitrobenzenesulfonyl)-1,4,7-triazacyclotetra-decanyl]-1,4-phenylenebis(methylene)]-N-(2-nitrobenzenesulfonyl)-2-(aminomethyl)pyridine A mixture of 1,7-bis(2-nitrobenzenesulfonyl)-1,4,7-triazacyclotetradecane (1.1 g, 1.9 mmol), the chloride from above (0.98 g, 2.3 mmol) and $K_2CO_3$ (0.85 g, 6.2 mmol) were heated to reflux in $CH_3CN$ (30 mL) under nitrogen for 62 h. The solvent was evaporated in vacuo and the residue was partitioned between $CH_2Cl_2$ (100 mL) and brine (70 mL). The aqueous phase was separated and extracted with $CH_2Cl_2$ (40 mL) and the combined organic extracts were dried ($MgSO_4$) and concentrated in vacuo. The residue was purified by column chromatography on silica gel (3% MeOH/$CH_2Cl_2$) and the evaporated fractions containing the desired product were subjected to a second column purification on silica gel (ethyl acetate) to give a pale yellow amorphous solid (940 mg, 49%): $^1H$ NMR ($CDCl_3$) δ 1.44 (br s, 6H), 1.60 (br s, 4H), 2.75 (m, 4H), 3.23–3.33 (m, 8H), 3.59 (s, 2H), 4.58 (s, 2H), 4.59 (s, 2H), 7.08–7.20 (m, 6H), 7.55–7.70 (m, 10H), 7.82 (dd, 2H, J=7.6, 1.6 Hz), 7.99 (d, 1H, J=7.8 Hz), 8.40 (d, 1H, J=4.7 Hz).

N-[4-(1,4,7-Triazacyclotetra-decanyl)-1,4-phenylenebis(methylene)]-2-(aminomethyl)pyridine pentahydrobromide dihydrate The intermediate from above (870 mg, 0.90 mmol), $K_2CO_3$ (1.15 g, 8.32 mmol), and thiophenol (0.33 mL, 3.2 mmol) were stirred in DMF (12 mL) for 7.5 h at room temperature. The mixture was concentrated in vacuo and the residue was partitioned between $CH_2Cl_2$ (30 mL) and $H_2O$ (15 mL). The organic phase was separated, washed with 5% $NaHCO_3$ (10 mL) then $H_2O$ (10 mL) then dried ($MgSO_4$) and concentrated in vacuo. The yellow residue was purified by column chromatography on basic alumina ($CH_2Cl_2$, 1% MeOH/$CH_2Cl_2$, and 10% MeOH/$CH_2Cl_2$) to give the free base as a yellow oil (134 mg, 36%): $^1H$ NMR ($CDCl_3$) δ 1.48 (br s, 6H), 1.60 (br s, 4H), 2.61 (m, 12H), 3.56 (s, 2H), 3.83 (s, 2H), 3.92 (s, 2H), 7.16 (m, 1H), 7.24 (m, 2H), 7.32 (m, 3H), 7.79 (m, 1H), 8.56 (d, 1H, J=4.7 Hz).

The free base (134 mg, 0.33 mmol) was dissolved in EtOH (4 mL) and a freshly prepared solution of saturated HBr(g) in EtOH (9 mL) was added, giving a white precipitate. The mixture was stirred for 5 min and diethyl ether (15 mL) was added. The precipitate was allowed to settle to the bottom of the flask and the supernatant solution was decanted. The solid was then dissolved in MeOH (5 mL) and re-precipitated with a large volume of ether, washed with ether by decantation (15×) and finally, the last traces of ether were removed by evaporation at reduced pressure (room temperature). Drying the solid in vacuo at 40° C. for 16 h, gave the desired product as a white solid (178 mg, 63%): $^1H$ NMR (DMSO-$d_6$) δ 1.44 (br s, 6H), 1.75 (br s, 4H), 3.04 (br s, 8H), 3.37 (m, 4H), 4.06 (br s, 2H), 4.31 (s, 2H), 4.38 (s, 2H), 7.52–7.68 (m, 6H), 8.01 (m, 1H), 8.70 (d, 1H, J=5.0 Hz); FAB-MS m/z 492 (MH+$H^{81}$Br), 490 (MH+$H^{79}$Br), 410 (M+H). Anal. Calcd for $C_{25}H_{39}N_5$.5HBr0.1$Et_2O$.2.3$H_2O$: C, 35.35; H, 5.79; N, 8.11; Br 46.29. Found: C, 35.55; H, 5.70; N, 8.18; Br, 46.17.

EXAMPLE 14

N-[7-(4,7,10,17-Tetraazabicyclo[13.3.1]heptadeca-1(17),13,15-trienyl)-1,4-phenylenebis(methylene)]-2-(aminomethyl)pyridine (AMD 7050)

2,6-Bis(2-aminoethyl)pyridine was prepared as described in Bridger et al. U.S. Pat. No. 5,698,546, which is hereby incorporated in its entirety by reference herein.

2,6-Bis[N-(2-nitrobenzenesulfonyl)-2-aminoethyl]pyridine

To a stirred solution of 2,6-Bis(2-aminoethyl)pyridine (2.7 g, 16 mmol) and $Et_3N$ (5.7 mL, 41 mmol) in $CH_2Cl_2$ (35 mL) was added 2-nitrobenzenesulfonyl chloride (8.01 g, 36.1 mmol) in CH$_2$Cl$_2$ (20 mL) and the mixture was stirred at room temperature under nitrogen for 42 h. The mixture was washed with brine (25 mL) and the organic phase was dried (MgSO$_4$) and concentrated in vacuo. The brown residue was purified by column chromatography on silica gel (50% then 60% THF/hexane) to give a pale yellow solid (5.2 g, 59%): $^1$H NMR (CDCl$_3$) δ 3.01 (m, 4H), 3.52 (m, 4H), 6.38 (m, 2H), 6.94 (d, 2H, J=7.7, Hz), 7.47 (t, 1H, J=7.7 Hz), 7.72 (m, 4H), 7.82 (m, 2H), 8.13 (m, 2H).

7-Diethoxyphosphoryl-4,10-Bis(2-nitrobenzenesulfonyl)-4,7,10,17-tetraazabicyclo[13.3.1]heptadeca-1(17),13,15-triene Using General Procedure D: Reaction of 2,6-bis[N-(2-nitrobenzenesulfonyl)-2-aminoethyl]pyridine (5.2 g, 9.7 mmol) and N-(diethoxyphosphoryl)-O,O'-bis(2-methylsulfonyl)di-ethanolamine (4.25 g, 10.7 mmol) followed by silica gel column purification (60% then 90% THF/hexane) of the reaction products gave the title compound as a yellow amorphous solid (1.48 g, 21%): $^1$H NMR (CDCl$_3$) δ 1.23 (t, 6H, J=7.1 Hz), 2.60 (m, 4H), 2.98–3.08 (m, 8H), 3.84–3.94 (m, 8H), 7.11 (d, 2H, J=7.6 Hz), 7.56–7.74 (m, 7H), 8.07 (m, 2H).

4,10-Bis(2-nitrobenzenesulfonyl)-4,7,10,17-tetraazabicyclo[13.3.1]heptadeca-1(17),13,15-triene Using General Procedure E: Reaction of 7-diethoxyphosphoryl-4,10-bis(2-nitrobenzenesulfonyl)-4,7,10,17-tetraazabicyclo[13.3.1]heptadeca-1(17),13,15-triene (1.04 g, 1.4 mmol) gave the title compound as a yellow amorphous solid (744 mg, 88%): $^1$H NMR (CDCl$_3$) δ 2.81 (m, 4H), 3.08 (m, 4H), 3.33 (m, 4H), 3.88 (m, 4H), 7.07 (d, 2H, J=7.7 Hz), 7.54–7.71 (m, 7H), 8.02 (m, 2H).

N-[7-[4,10-Bis(2-nitrobenzenesulfonyl)-4,7,10,17-tetraazabicyclo[13.3.1]heptadeca-1(17), 13,15-trienyl]-1,4-phenylenebis(methylene)]-N-(2-nitrobenzenesulfonyl)-2-(aminomethyl)pyridine Using General Procedure F: Reaction of 4,10-bis(2-nitrobenzenesulfonyl)-4,7,10,17-tetraazabicyclo[13.3.1]heptadeca-1(17),13,15-triene (740 mg, 1.2 mmol) and N-[1-methylene-4-(chloromethylene)phenylene]-N-(2-nitrobenzenesulfonyl)-2-(aminomethyl)pyridine (610 mg, 1.4 mmol) followed by silica gel column purification (50% then 80% THF/hexane) of the reaction products gave the title compound as a yellow amorphous solid (648 mg, 54%): $^1$H NMR (CDCl$_3$) δ 2.26 (m, 4H), 3.03 (m, 8H), 3.37 (s, 2H), 3.94 (m, 4H), 4.56 (s, 2H), 4.57 (s, 2H), 6.95–7.17 (m, 8H), 7.52–7.72 (m, 11H), 7.85 (m, 2H), 7.98 (d, 1H, J=7.7 Hz), 8.39 (d, 1H, J=4.8 Hz).

General Procedure G

N-[7-(4,7,10,17-Tetraazabicyclo[13.3.1]heptadeca-1(17),13,15-trienyl)-1,4-phenylenebis(methylene)]-2-(aminomethyl)pyridine Hexahydrobromide Trihydrate To a solution of N-[7-[4,10-bis(2-nitrobenzenesulfonyl)-4,7,10,17-tetraazabicyclo[13.3.1]heptadeca-1(17),13,15-trienyl]-1,4-phenylenebis(methylene)]-N-(2-nitrobenzenesulfonyl)-2-(aminomethyl)pyridine (640 mg, 0.64 mmol) in DMF (9 mL) containing K$_2$CO$_3$ (806 mg, 5.83 mmol) was added thiophenol (0.24 mL, 2.3 mmol) and the mixture was stirred at room temperature for 2 h. The mixture was concentrated in vacuo and the residue partitioned between ethyl acetate (30 mL) and water (10 mL). The organic phase was separated and extracted with 5% NaHCO$_3$ (3×5 mL) then brine (5 mL). The combined aqueous phases were extracted with CH$_2$Cl$_2$ (3×10 mL). The combined organic extracts were dried (MgSO$_4$) and evaporated and the residue was purified by column chromatography on alumina (CH$_2$Cl$_2$ followed by 10% MeOH/CH$_2$Cl$_2$) to give the free base of the title compound as a yellow oil (83 mg, 29%): $^1$H NMR (CDCl$_3$) δ 2.57 (m, 8H), 3.01 (s, 8H), 3.36 (s, 2H), 3.78 (s, 2H), 3.92 (s, 2H), 6.64 (d, 2H, J=8.0 Hz), 7.07 (m, 4H), 7.18 (m, 1H), 7.33 (d, 1H, J=7.7 Hz), 7.67 (m, 2H), 8.58 (d, 1H, J=4.8 Hz).

The free base (74 mg, 0.17 mmol) was dissolved in MeOH (3 mL) and a freshly prepared solution of saturated HBr(g) in MeOH (7 mL) was added giving a white precipitate. The mixture was stirred for 5 min and diethyl ether was added (10 mL), the solid was allowed to settle to the bottom of the flask and the supernatant solution decanted. The solid was washed by decantation with MeOH (5×5 mL) then ether (10×5 mL) and the last traces of ether were removed by evaporation in vacuo followed by drying in vacuo at 40° C. for 17.5 h to give the title compound as a white solid (153 mg, 93%): $^1$H NMR (DMSO-d$_6$) δ 2.81 (br s, 4H), 3.28 (m, 8H), 3.61 (br s, 4H), 3.85 (s, 2H), 4.27 (s, 2H), 4.36 (s, 2H), 7.29 (d, 2H, J=7.7 Hz), 7.36 (d, 2H, J=7.7 Hz), 7.53 (m, 3H), 7.63 (d, 1H, J=7.7 Hz), 7.80 (t, 1H, J=7.7 Hz), 7.99 (m, 1H), 8.69 (d, 1H, J=5.3 Hz); FAB-MS m/z 527 (MH+H$^{81}$ Br), 525 (MH+H$^{79}$Br), 445 (M+H). Anal. Calcd for C$_{27}$H$_{36}$N$_6$.6HBr 3H$_2$O: C, 32.95; H, 4.92; N, 8.54; Br, 48.72. Found: C, 32.75; H, 4.89; N, 8.39; Br, 48.61.

EXAMPLE 15

N-[7-(4,7,10-Triazabicyclo[13.31]heptadeca-1 (17), 13,15-trienyl)-1,4-phenylenebis(methylene)]-2-(aminomethyl)pyridine (AMD 7051)

1,3-Phenylenebis(ethylene)diamine

To a solution of 1,3-phenylenediacetonitrile (9.37 g, 60 mmol) in CH$_3$OH (saturated with NH$_3$,150 mL) was added Raney-Ni (ca. 20 g, previously washed with CH$_3$OH several times) and the mixture was hydrogenated at 45 psi on a Parr apparatus for 48 h. The reaction mixture was filtered through celite and the filtrate evaporated to give the crude product (9.45 g, 96%) as a light green oil: $^1$H NMR (CDCl$_3$) δ 0.80–1.50 (br s, 4H), 2.70–2.76 (m, 4H), 2.94–2.99 (m, 4H), 7.01–7.07 (m, 3H), 7.18–7.26 (m, 1H). This was used in the next step without further purification.

N,N'-Bis(2-Nitrobenzenesulfonyl)-1,3-Phenylenebis(ethylene)diamine

A solution of 2-nitrobenzenesulfonylchloride (19.94 g, 0.090 mol) in dry CH$_2$Cl$_2$ (70 mL) was added dropwise via cannula to a stirred solution of 1,3-phenylenebis(ethylene)diamine (4.92 g, 0.030 mol) and Et$_3$N (16.7 mL, 0.12 mol) in dry CH$_2$Cl$_2$ (80 mL) under nitrogen. The reaction mixture was stirred overnight at room temperature, and then quenched with water (20 mL). The precipitate was collected by filtration and washed with H$_2$O, CH$_3$OH, and Et$_2$O to give the desired product (9.22 g, 58%) as a white solid: $^1$H NMR (DMSO-d$_6$) δ 2.66 (t, 4H, J=7.7 Hz), 3.08–3.18 (br s, 4H), 6.94 (d, 2H, J=6.4 Hz), 6.98 (s, 1H), 7.12 (dd, 1H, J=6.4, 6.4 Hz), 7.78–7.84 (br m, 4H), 7.90–7.64 (br m, 4H), 8.16 (br s, 2H).

7-Diethoxyphosphoryl-4,10-bis(2-nitrobenzenesulfonyl)-4,7,10-triazabicyclo[13.3.1]heptadeca-1(17),13,15-triene Using General Procedure D: Reaction of N,N'-bis(2-nitrobenzenesulfonyl)-1,3-phenylenebis(ethylene)diamine (8.74 g, 16.4 mmol) with N-(diethoxyphosphoryl)-O,O'-bis (2-methylsulfonyl)di-ethanolamine (6.50 g, 16.4 mmol) followed by silica gel column purification of the reaction products (1:15:35 CH$_3$OH—Et$_2$O—CH$_2$Cl$_2$) gave the title compound (4.03 g, 33%) as a yellow foam: $^1$H NMR (CDCl$_3$) δ 1.21 (t, 6H, J=6.4 Hz), 2.39–2.46 (br m, 4H), 2.83–2.97 (br m, 8H), 3.68–3.72 (m, 4H), 3.80–3.92 (m, 4H), 7.16 (d, 2H, J=6.5 Hz), 7.18 (s, 1H), 7.24 (dd, 1H, J=6.5, 6.5 Hz), 7.60–7.74 (m, 6H), 8.04–8.08 (m, 2H).

4,10-Bis(2-nitrobenzenesulfonyl)-4,7,10-triazabicyclo[13.3.1]heptadeca-1(17),13,15-triene Using General Procedure E: Reaction of 7-diethoxyphosphoryl-4,10-bis(2-nitrobenzenesulfonyl)-4,7,10-triazabicyclo[13.3.1]heptadeca-1(17),13,15-triene (1.27 g, 1.72 mmol) followed by silica gel column purification of the reaction products (1:15:25 CH$_3$OH—EtOAc—CH$_2$Cl$_2$ then 20% CH$_3$OH in CH$_2$Cl$_2$) gave the title compound (574 mg, 57%/O) as a light yellow foam: $^1$H NMR (CDCl$_3$) δ 1.42–1.50 (br, 1H), 2:01 (t, 4H, J=5.4 Hz), 2.90–3.10 (br m, 4H), 3.08 (t, 4H, J=5.4 Hz), 3.56–3.60 (br m, 4H), 7.16 (d, 2H, J=6.8 Hz), 7.31 (dd, 1H, J=6.8, 6.8 Hz), 7.36 (s, 1H), 7.61–7.63 (m, 2H), 7.70–7.73 (m, 4H), 8.01–8.04 (m, 2H).

N-[7-[4,10-Bis(2-nitrobenzenesulfonyl)-4,7,10-triazabicyclo[13.3.1]heptadeca-1 (17),13,15-trienyl]-1,4-phenylenebis(methylene)]-N-(2-Nitrobenzenesulfonyl)-2-(aminomethyl)pyridine Using General Procedure F: Reaction of 4,10-bis(2-nitrobenzenesulfonyl)-4,7,10-triazabicyclo[13.3.1]heptadeca-1(17),13,15-triene (420 mg, 0.7 mmol) with N-[1-methylene-4-(chloromethylene)phenylene]-N-(2-nitrobenzenesulfonyl)-2-(aminomethyl)pyridine (302 mg, 0.7 mmol) followed by silica gel column purification of the reaction products (1:3 Et$_2$O—CH$_2$Cl$_2$) gave the title compound (491 mg, 70%) as a pale yellow solid: $^1$H NMR (CDCl$_3$) δ 1.97–2.02 (br m, 4H), 2.73–2.78 (br m, 4H), 2.90–2.94 (br m, 4H), 3.32 (s, 2H), 3.64–3.67 (br m, 4H), 4.55 (s, 2H), 4.58 (s, 2H), 6.93 (d, 2H, J=8.0 Hz), 7.04 (d, 2H, J=8.0 Hz), 7.09–7.16 (br m, 4H), 7.23 (s, 1H), 7.29 (dd, 1H, J=7.9, 7.9 Hz), 7.51–7.72 (m, 10H), 7.80–7.83 (m, 2H), 7.98 (d, 1H, J=7.8 Hz), 8.39 (m, 1H).

N-[7-(4,7,10-Triazabicyclo[13.3.1]heptadeca-1(17),13,15-trienyl)-1,4-phenylenebis(methylene)]-2-(aminomethyl)pyridine Pentahydrobromide Dihydrate Using General Procedure G: Reaction of N-[7-[4,10-bis(2-nitrobenzenesulfonyl)-4,7,10-triazabicyclo[13.3.1]heptadeca-1(17),13,15-trienyl]-1,4-phenylenebis(methylene)]-N-(2-nitrobenzenesulfonyl)-2-(aminomethyl)pyridine (380 mg, 0.38 mmol) followed by basic alumina column purification of the reaction products (1:20 CH$_3$OH—CH$_2$Cl$_2$) gave the free base of the title compound.

Conversion of the free base to the hydrobromide salt using a saturated solution of HBr(g) in CH$_3$OH followed by drying in vacuo overnight, gave the title compound (110 mg, 34% overall) as a white solid: $^1$H NMR (DMSO-d$_6$) δ 2.80–2.88 (br s, 4H), 3.02–3.06 (br s, 4H), 3.10–3.16 (br s, 4H), 3.38–3.44 (br s, 4H), 3.80–3.86 (br s, 2H), 4.25–4.30 (br s, 2H), 4.33–4.37 (br s, 2H), 7.27–7.32 (br m, 4H), 7.42–7.63 (br m, 6H), 7.96 (dd, 1H, J=7.7, 7.7 Hz), 8.10–8.30 (br s, 3H), 8.69 (d, 1H, J=4.9 Hz), 9.45–9.62 (br s, 2H); FAB-MS m/z 526 (MH+H$^{81}$Br), 524 (MH+H$^{79}$Br), 444 (M+H, 100); Anal. Calcd for C$_{28}$H$_{42}$N$_5$Br$_5$.2H$_2$O: C, 38.03; H, 5.24; N, 7.92; Br, 45.18. Found: C, 38.37; H, 5.28; N, 7.76; Br, 45.36.

EXAMPLE 16

N-[1-(1,4,7-Triazacyclotetra-decanyl)-1,4-phenylenebis(methylene)]-2-(aminomethyl)pyridine (AMD 7059)

General Procedure H

4-Diethoxyphosphoryl-7-(2-nitrobenzenesulfonyl)-1,4,7-triazacyclotetradecane

To a stirred solution of 4-diethoxyphosphoryl-1,7-bis(2-nitrobenzenesulfonyl)-1,4,7-triazacyclotetradecane (1.32 g, 1.87 mmol) and K$_2$CO$_3$ (654 mg, 4.73 mmol) in DMF (11 mL) under nitrogen was added dropwise a solution of thiophenol (0.15 mL, 1.46 mmol) in DMF (8 mL) over 1 h. The mixture was stirred for an additional 3 h and then concentrated in vacuo. The residue was partitioned between CHCl$_3$ (50 mL) and H$_2$O (25 mL). The aqueous phase was separated and extracted with CHCl$_3$ (3×20 mL) and the combined organic extracts were dried (MgSO$_4$) and concentrated in vacuo. The residue was purified by column chromatography on basic alumina (CHCl$_3$ then 3% MeOH/CHCl$_3$) to give the title compound as a yellow oil (178 mg, 23%): $^1$H NMR (CDCl$_3$) δ 1.31 (t, 6H, J=7.0 Hz), 1.40–1.67 (m, 10H), 2.65 (m, 2H), 2.78 (m, 2H), 3.12 (m, 2H), 3.26–3.37 (m, 4H), 3.48 (m, 2H), 3.97–4.09 (m, 4H), 7.61 (m, 1H), 7.68 (m, 2H), 8.06 (m, 1H).

N-[1-[4-Diethoxyphosphoryl-7-(2-nitrobenzenesulfonyl)-1,4,7-triazacyclotetra-decanyl]-1,4-phenylenebis(methylene)]-N-(2-nitrobenzenesulfonyl)-2-(aminomethyl)pyridine Using General Procedure F: Reaction of 4-diethoxyphosphoryl-7-(2-nitrobenzenesulfonyl)-1,4,7-triazacyclotetradecane (236 mg, 0.453 mmol) and N-[1-methylene-4-(chloromethylene)phenylene]-N-(2-nitrobenzenesulfonyl)-2-(aminomethyl)pyridine (238 mg, 0.551 mmol) followed by silica gel column purification of the reaction products (50% then 80% THF/hexane) gave the title compound as a yellow amorphous solid (305 mg, 73%): $^1$H NMR (CDCl$_3$) δ 1.27 (t, 6H, J=7.1 Hz), 1.43 (br s, 8H), 1.63 (br s, 2H), 2.32 (br s, 2H), 2.55 (m, 2H), 3.13–3.41 (m, 8H), 3.49 (s, 2H), 3.85–4.02 (m, 4H), 4.57 (s, 2H), 4.58 (s, 2H), 7.07–7.22 (m, 6H), 7.51–7.71 (m, 7H), 7.98 (d, 1H, J=7.4 Hz), 8.04 (m, 1H), 8.41 (d, 1H, J=4.0 Hz).

N-[1-[7-(2-Nitrobenzenesulfonyl)-1,4,7-triazacyclotetra-decanyl]-1,4-phenylenebis(metylene)]-N-(2-nitrobenzenesulfonyl)-2-(aminomethyl)pyridine Using General Procedure E: Reaction of N-[1-[4-diethoxyphosphoryl-7-(2-nitrobenzenesulfonyl)-1,4,7-triazacyclotetra-decanyl]-1,4-phenylenebis(methylene)]
(2-nitrobenzenesulfonyl)-2-(aminomethyl)pyridine (300 mg, 0.328 mmol) gave the title compound as a yellow amorphous solid (214 mg, 84%): $^1$H NMR (CDCl$_3$) δ 1.34–1.44 (m, 8H), 1.69 (br s, 2H), 2.34 (m, 2H), 2.52 (m, 2H), 2.62 (m, 2H), 2.82 (m, 2H), 3.42 (m, 6H), 4.58 (s, 2H), 4.59 (s, 2H), 7.08–7.24 (m, 6H), 7.52–7.71 (m, 7H), 8.01 (m, 2H), 8.42 (d, 1H, J=4.1 Hz).

N-[1-(1,4,7-Triazacyclotetra-decanyl)-1,4-phenylenebis(methylene)]-2-(aminomethyl)pyridine Pentahydrobromide Dihydrate A mixture of N-[1-[7-(2-nitrobenzenesulfonyl)-1,4,7-triazacyclotetra-decanyl]-1,4-phenylenebis(methylene)]-N-(2-nitrobenzenesulfonyl)-2-(aminomethyl)pyridine (209 mg, 0.268 mmol), K$_2$CO$_3$ (298 mg, 2.16 mmol), and thiophenol (0.17 mL, 1.7 mmol) in acetonitrile (3 mL) were heated to 50° C. for 16.5 h. The reaction mixture was diluted with CH$_2$Cl$_2$ (10 mL) and washed with brine (10 mL). The separated aqueous phase was extracted with CH$_2$Cl$_2$ (3×5 mL) and the combined organic extracts were dried (MgSO$_4$) and evaporated. The residue was purified by column chromatography on basic alumina (CHCl$_3$ then 10% MeOH/ CHCl$_3$) to give the free base of title compound as a yellow oil (92 mg, 84%): $^1$H NMR (CDCl$_3$) δ 1.21–1.62 (m, 10H), 2.40–2.49 (m, 4H), 2.60 (m, 6H), 2.79 (m, 2H), 3.49 (s, 2H), 3.80 (s, 2H), 3.91 (s, 2H), 7.14 (m, 1H), 7.28 (m, 5H), 7.62 (m, 1H), 8.54 (d, 1H, J=4.4 Hz).

Conversion of the free base (86 mg, 0.21 mmol) to the hydrobromide salt using a saturated solution of HBr(g) in MeOH (See General Procedure G) followed by drying in vacuo at 40° C. for 15.5 h gave the title compound as a white solid (128 mg, 70%): $^1$H NMR (D$_2$O) δ 1.48 (br s, 61), 1.82 (m, 4H), 3.22–3.36 (m, 10H), 3.50 (br s, 2H), 4.48 (s, 4H), 4.64 (s, 2H), 7.62 (s, 4H), 7.88 (m, 1H), 7.94 (d, 1H, J=8.0 Hz), 8.38 (m, 1H), 8.77 (d, 1H, J=5.2 Hz); FAB-MS m/z 492 (MH+H$^{81}$Br), 490 (M+H$^{79}$Br), 410 (M+H). Anal. Calcd for C$_{25}$H$_{39}$N$_5$.5HBr 2.5H$_2$O.0.1Et$_2$O: C, 35.20; H, 5.82; N, 8.08; Br, 46.10. Found: C, 35.48; H, 5.66; N, 8.10; Br, 46.05.

EXAMPLE 17

N-[4-[4,7,10,17-Tetraazabicyclo[13.3.1]heptadeca-1(17), 13,15-trienyl]-1,4-phenylenebis(methylene)]-2-(aminomethyl)pyridine (AMD 7063)

7-Diethoxyphosphoryl-10-(2-nitrobenzenesulfonyl)-4,7, 10,17-tetraazabicyclo[13.3.1]heptadeca-1(17),13,15-triene Using General Procedure H: Reaction of 7-diethoxyphosphoryl 4,10-bis(2-nitrobenzenesulfonyl)-4, 7,10,17-tetraazabicyclo[13.3.1]heptadeca-1(17),13,15-triene (1.48 g, 2.00 mmol) with thiophenol (with an additional heating of the reaction mixture to 50° C. for 1.5 h after the addition) followed by silica gel column purification of the reaction products (8% MeOH/CHCl$_3$) gave the title compound as a light yellow oil (423 mg, 52%): $^1$H NMR (CDCl$_3$) δ 1.23 (t, 6H, J=7.0 Hz), 2.50 (br s, 2H), 2.79 (br s, 2H), 3.02–3.15 (m, 1OH), 3.82–3.98 (m, 6H), 7.06 (d, 2H, J=7.6 Hz), 7.54–7.63 (m, 2H), 7.70 (m, 2H), 8.01 (br s, 1H).

N-[4-[7-Diethoxyphosphoryl-10-(2-nitrobenzenesulfonyl)-4,7,10,17-tetraazabicyclo[13.3.1] heptadeca-1 (17),13,15-trienyl]-1,4-phenylenebis (methylene)]-N-(2-nitrobenzenesulfonyl)-2-(aminomethyl) pyridine Using General Procedure F: Reaction of 7-diethoxyphosphoryl-10-(2-nitrobenzenesulfonyl)-4,7,10, 17-tetraazabicyclo[13.3.1]heptadeca-1(17),13,15-triene (410 mg, 0.738 mmol) and N-[1-methylene-4-(chloromethylene)phenylene]-N-(2-nitrobenzenesulfonyl)-2-(amninomethyl)pyridine (397 mg, 0.919 mmol) followed by silica gel column purification of the reaction products (50%, 80%, and 90% THF/hexane) gave the title compound as a white amorphous solid (441 mg, 63%): $^1$H NMR (CDCl$_3$) δ 1.15 (t, 6H, J=7.0 Hz), 2.42 (m, 4H), 2.77 (m, 2H), 2.92–3.02 (m, 6H), 3.10 (m, 2H), 3.59 (s, 2H), 3.66–3.91 (m, 6H), 4.58 (s, 2H), 4.59 (s, 2H), 6.94 (d, 1H, J=7.6 Hz), 7.07–7.14 (m, 6H), 7.22 (d, 1H, J=7.8 Hz), 7.51–7.72 (m, 8H), 8.00 (d, 1H, J=7.8 Hz), 8.04 (m, 1H), 8.42 (d, 1H, J=4.0 Hz).

N-[4-[7-Diethoxyphosphoryl-4,7,10,17-tetraazabicyclo [13.3.1]heptadeca-1 (17),13,15-trienyl]-1,4-phenylenebis (methylene)]-N-2-(aminomethyl)pyridine A mixture of N-[4-[7-diethoxyphosphoryl-10-(2-nitrobenzenesulfonyl)-4,7,10,17-tetraazabicyclo[13.3.1] heptadeca-1(17),13,15-trienyl]-1,4-phenylenebis (methylene)]-N-(2-nitrobenzenesulfonyl)-2-(aminomethyl) pyridine (434 mg, 0.456 mmol), K$_2$CO$_3$ (508 mg, 3.68 mmol), and thiophenol (0.28 mL, 2.7 mmol) were heated to 50° C. in CH$_3$CN (3.5 mL) under nitrogen for 15 h. Upon cooling, the reaction mixture was partitioned between CHCl$_3$ (15 mL) and brine (15 mL) and the aqueous layer was separated and extracted with CHCl$_3$ (3×5 mL). The combined organic extracts were dried (MgSO$_4$) and concentrated in vacuo and the residue was purified by column chromatography on basic alumina (CHCl$_3$ then 10% MeOH/ CHCl$_3$) to give a yellow oil (218 mg, 82%): $^1$H NMR (CDCl$_3$) δ 1.16 (t, 6H, J=7.1 Hz), 2.35 (m, 2H), 2.55 (m, 2H), 2.75 (m, 2H), 2.82 (m, 2H), 2.96–3.08 (m, 6H), 3.16 (m, 2H), 3.68 (s, 2H), 3.69–3.88 (m, 4H), 3.82 (s, 2H), 3.93 (s, 2H), 6.95 (d, 1H, J=7.6 Hz), 7.00 (d, 1H, J=7.5 Hz), 7.15–7.34 (m, 6H), 7.50 (m, 1H), 7.65 (m, 1H), 8.56 (d, 1H, J=4.7 Hz).

N-[4-[4,7,10,17-Tetraazabicyclo[13.3.1]heptadeca-1(17), 13,15-trienyl]-1,4-phenylenebis(methylene)]-2-(aminomethyl)pyridine Hexahydrobromide Hydrate To a stirred solution of N-[4-[7-diethoxyphosphoryl-4,7, 10,17-tetraazabicyclo[13.3.1]heptadeca-1 (17),13,15-trienyl]-1,4-phenylenebis(methylene)]-N-2-(aminomethyl) pyridine (211 mg, 0.36 mmol) in acetic acid (0.6 mL) was added a freshly prepared solution of saturated HBr(g) in acetic acid (6 mL) and the reaction mixture was allowed to stir at room temperature for 4 h. Addition of diethyl ether (10 mL) gave a white precipitate that was allowed to settle to the bottom of the flask and the supernatant solution was decanted. The solid was washed by decantation with MeOH (4×5 mL) and ether (6×5 mL) and the remaining traces of ether were removed by evaporation under reduced pressure. The product was dried in vacuo at 40° C. for 17 h, to give the title compound as a pale yellow solid (223 mg, 63%): $^1$H NMR (D$_2$O) δ 3.14–3.36 (m, 10H), 3.55 (m, 4H), 3.75 (m, 2H), 4.45 (s, 2H), 4.50 (s, 2H), 4.64 (s, 2H), 7.22 (m, 2H), 7.53 (s, 4H), 7.70 (m, 1H), 7.95 (m, 1H), 8.00 (d, 1H, J=7.9 Hz), 8.46 (m, 1H), 8.79 (d, 1H, J=3.9 Hz); FAB-MS m/z 527 (MH+H$^{81}$Br), 525 (MH+H$^{79}$Br), 445 (M+H). Anal. Calcd for C$_{27}$H$_{36}$N$_6$.6HBr.1.5H$_2$O.0.2Et$_2$O: C, 34.35; H, 4.87; N, 8.65; Br, 49.33. Found: C, 34.57; H, 5.04; N, 8.68; Br, 49.09.

EXAMPLE 18

N-[4-[4,7,10-Triazabicyclo[13.3.1]heptadeca-1 (17), 13,15-trienyl]-1,4-phenylenebis(methylene)]-2-(aminomethyl)pyridine (AMD 7058)

7-Diethoxyphosphoryl-10-(2-nitrobenzenesulfonyl)-4,7, 10-10 triazabicyclo[13.3.1]heptadeca-1(17),13,15-triene Using General Procedure H: Reaction of 7-diethoxyphosphoryl-4,10-bis(2-nitrobenzenesulfonyl)-4, 7,10-triazabicyclo[13.3.1]heptadeca-1(17),13,15-triene (1.11 g, 1.5 mmol) followed by silica gel column purification of the reaction products (2:5:20 CH$_3$OH—Et$_2$O—CH$_2$Cl$_2$ then 1:5 CH$_3$OH—CH$_2$Cl$_2$) gave the title compound as a pale yellow oil (300 mg, 54%): $^1$H NMR (CDCl$_3$) δ 1.21 (t, 6H, J=7.1 Hz), 1.78–1.92 (br s, 1H), 2.31–2.38 (br m, 2H), 2.56–2.60 (br m, 2H), 2.81–2.98 (br m, 10H), 3.60–3.64 (br m, 2H), 3.75–3.91 (m, 4H), 7.05–7.12 (m, 2H), 7.24–7.29 (m, 2H), 7.60–7.63 (m, 1H), 7.68–7.71 (m, 2H), 8.02–8.06 (m, 1H).

N-[4-[7-Diethoxyphosphoryl-10-(2-nitrobenzenesulfonyl)-4,7,10-20 triazabicyclo[13.3.1] heptadeca-1(17),13,15-trienyl]-1,4-phenylenebis (methylene)]-N-(2-nitrobenzenesulfonyl)-2-(aminomethyl) pyridine Using General Procedure F: Reaction of 7-diethoxyphosphoryl-10-(2-nitrobenzenesulfonyl)-4,7,10- triazabicyclo[13.3.1]heptadeca-1(17),13,15-triene (290 mg, 0.52 mmol) with N-[1-methylene-4-(chloromethylene)phenylene]-N-(2-25 nitrobenzenesulfonyl)-2-(aminomethyl)pyridine (271 mg, 0.63 mmol) followed by silica gel column purification of the reaction products (1:12:12 $CH_3OH$—$Et_2O$—$CH_2Cl_2$) gave the title compound (298 mg, 60%) as a pale yellow solid: $^1H$ NMR ($CDCl_3$) δ 1.17 (t, 6H, J=7.0 Hz), 2.29–2.45 (br m, 4H), 2.55–2.65 (br m, 2H), 2.71–2.75 (br s, 4H), 2.85–2.91 (br m, 2H), 2.96–2.98 (br m, 2H), 3.57 (s, 2H), 3.67–3.84 (br m, 6H), 4.57–4.61 (br s, 4H), 7.07–7.28 (br m, 10H), 7.55–7.71 (br m, 7H), 7.99–8.02 (m, 2H), 8.42–8.46 (m, 1H).

N-[4-[10-(2-Nitrobenzenesulfonyl)-4,7,10-triazabicyclo[13.3.1]heptadeca-1(17),13,15-trienyl]-1,4-phenylenebis(methylene)]-N-(2-nitrobenzenesulfonyl)-2-(aminomethyl)pyridine Using General Procedure E: Reaction of N-[4-[7-diethoxyphosphoryl-10-(2-nitrobenzenesulfonyl)-4,7,10-triazabicyclo[13.3.1]heptadeca-1 (17),13,15-trienyl]-1,4-phenytenebis(methylene)]-N-(2-nitrobenzenesulfonyl)-2-(aminomethyl)pyridine (290 mg, 0.31 mmol) gave the title compound (240 mg, 95%) as a white solid: $^1H$ NMR ($CDCl_3$) δ 1.65–1.79 (br s, 1H, coincide with $H_2O$ peak), 2.15–2.19 (br m, 4H), 2.44–2.48 (br m, 2H), 2.61–2.65 (br m, 2H), 2.67–2.71 (br m, 2H), 3.00–3.04 (br m, 2H), 3.10–3.14 (br m, 2H), 3.56–3.60 (br s, 4H), 4.55 (s, 2H), 4.61 (s, 2H), 6.96 (d, 1H, J=7.8 Hz), 7.02–7.10 (br m, 6H), 7.22–7.28 (br m, 3H), 7.52–7.72 (br m, 7H), 7.96–7.99 (m, 2H), 8.42–8.46 (m, 1H). This was used without further purification.

N-[4-[4,7,10-Triazabicyclo[13.3.1]heptadeca-1(17),13, 15-trienyl]-1,4-phenylenebis(methylene)]-2-(aminomethyl)pyridine Pentahydrobromide Dihydrate Using General Procedure G: Reaction of N-[4-[10-(2-nitrobenzenesulfonyl)-4,7,10-triazabicyclof 13.3.1) heptadeca-1(17),13,15-trienyl]-1,4-phenylenebis(methylene)]-N-(2-nitrobenzenesulfonyl)-2-(aminomethyl)pyridine (236 mg, 0.29 mmol) followed by alumina column purification of the reaction products (1:99 $CH_3OH$—$CH_2Cl_2$ then 1:10 $CH_3OH$—$CH_2Cl_2$) gave the free base of the title compound (111 mg, 86%) as a pale yellow oil: $^1H$ NMR ($CDCl_3$) δ 2.24–2.28 (br s, 3H), 2.43–2.50 (br m, 4H), 2.58–2.62 (br m, 2H), 2.73–2.79 (br m, 8H), 2.95–2.98 (br m, 2H), 3.50 (s, 2H), 3.77 (s, 2H), 3.90 (s, 2H), 6.83–6.87 (br m, 3H), 7.05–7.33 (br m, 7H), 7.63–7.67 (m, 1H), 8.54–8.56 (m, 1H).

Conversion of the free base (104 mg, 0.23 mmol) to the hydrobromide salt using a saturated solution of HBr(g) in $CH_3OH$ followed by drying of the product in vacuo, gave the title compound (101 mg, 52%) as a white solid: $^1H$ NMR $D_2O$) δ 2.90–2.94 (br m, 2H), 2.97–3.01 (br m, 2H), 3.12–3.16 (br m, 2H), 3.17–3.21 (br m, 2H), 3.24–3.28 (br m, 4H), 3.47–3.51 (br m, 2H), 3.57–3.61 (br m, 2H), 4.38–4.42 (m, 6H), 7.34–7.40 (m, 2H), 7.46–7.60 (m, 8H), 7.90–7.94 (m, 1H), 8.58–8.62 (m, 1H); FAB-MS m/z 526 (MH+$H^{81}$Br), 524 (MH+$H^{79}$Br), 444 (M+H, 100); Anal. Calcd. for $C_{28}H_{42}N_5Br.2.5H_2O$: C, 37.65; H, 5.30; N, 7.84; Br, 44.73. Found: C, 37.53; H, 5.26; N, 7.79; Br, 44.75.

TABLE 2

| Compound | Inhibition of mAb 12G5 binding $IC_{50}{}^a$ (ng/ml) |
|---|---|
| AMD3100 | 27 |
| AMD3465 | 3 |
| AMD7049 | 52 |
| AMD7050 | 1 |

TABLE 2-continued

| Compound | Inhibition of mAb 12G5 binding $IC_{50}{}^a$ (ng/ml) |
|---|---|
| AMD7051 | 7 |
| AMD7058 | >1000 |
| AMD7059 | >1000 |
| AMD7063 | 9 |
| SDF-1α[b] | 270 |

[a]Inhibition of mAb 12G5 binding to CXCR-4 in SUP-T1 cells.
[b]Natural ligand for CXCR-4 (Bleul et al. Nature, 382: 829–832 (1996); Oberlin et al., Nature, 382: 833–835 (1996)).

TABLE 3

| Compound | % Inhibition of $Ca^{2+}$ flux (conc) or $IC_{50}{}^a$ (ng/ml) |
|---|---|
| AMD3100 | 5 |
| AMD3465 | 1 |
| AMD7049 | 100% (1 μg/ml) |
| AMD7050 | 100% (1 μg/ml) |
| AMD7051 | 100% (1 μg/ml) |
| AMD7058 | 44% (1 μg/ml) |
| AMD7059 | 36% (1 μg/ml) |
| AMD7063 | 100% (1 μg/ml) |

[a]Inhibition of Signal transduction (increasing intracellular $Ca^{2+}$ flux) induced by SDF-1α binding to CXCR-4 on SUP-T1 cells.

Each of the following compounds, including AMD 3484 (see FIG. 1AB), were synthesized according to procedures in Bridger et at., *J. Med. Chem.* 1995, 38, 366–378; *J. Med. Chem.* 1996, 39, 109–119 and U.S. Pat. No. 5,583,131, U.S. Pat. No. 5,698,546 and allowed copending U.S. patent application Ser. No. 08/659,500, which are each incorporated in their entirety by reference herein.

EXAMPLE 19

1-[2,6-Dimethoxypyrid-4-yl(methylene)]-1,4,8,11-tetraazacyclotetradecane Tetrahydrobromide (AMD 7032)

$^1H$ NMR ($D_2O$) δ 1.78 (m, 2H), 1.88–1.92 (m, 2H), 2.59–3.03 (m, 16H), 3.60 (s, 2H), 3.91 (s, 6H), 6.44 (s, 2H); $^{13}C$ NMR ($D_2O$) δ 26.75, 27.91, 48.34, 49.21, 49.89, 50.96, 52.01, 52.86, 54.88, 57.15, 57.53, 59.42, 142.65, 157.42, 166.42; FAB MS m/z 352 (M+H); Anal. ($C_{18}H_{33}N_5O_2$4.1 HBr 0.25 $H_2O$); Calc. C, 31.44; H, 5.51; N, 10.18; Br, 47.64. Found C, 31.17; H, 5.61; N, 9.92; Br, 47.54.

EXAMPLE 20

1-[2-Chloropyrid-4-yl(methylene)]-1,4,8,11-tetraazacyclotetradecane Tetrahydrochloride Monohydrate (AMD 7048)

$^1H$ NMR ($D_2O$) δ 1.92 (m, 2H), 2.12 (m, 2H), 2.77–2.80 (m, 4H), 2.96–3.39 (m, 12H), 3.85 (s, 2H), 7.33 (d, 1H, J=5.4 Hz), 7.44 (s, 1H), 8.40 (d, 1H, J=5.4 Hz); $^{13}C$ NMR ($D_2O$) δ 24.75, 27.59, 47.40, 47.55, 49.11, 49.23, 52.12, 52.40, 53.81, 54.42, 56.98, 126.97, 128.30, 151.90, 152.34, 153.78; FAB MS m/z 326 (M+H); Anal. ($C_{16}H_{28}N_5Cl4.2HCl0.5HOAc.1.1H_2O$); Calc. C, 38.61; H, 6.94; N, 13.24; Cl, 34.86. Found C, 38.63; H, 6.94; N, 13.52; Cl, 34.61.

EXAMPLE 21

1-[2,6-Dimethylpyrid-4-yl(methylene)]-1,4,8,11-tetraazacyclotetradecane Pentahydrobromide Dihydrate (AMD 7060)

$^1H$ NMR ($D_2O$) δ 1.77 (m, 2H), 1.93 (m, 2H), 2.48 (s, 6H), 2.61–3.00 (m, 16H), 3.61 (s, 2H), 7.07 (s, 2H); $^{13}C$

NMR (D$_2$O) δ 25.30, 26.22, 27.49, 47.75, 48.65, 49.43, 50.41, 51.58, 52.19, 54.09, 56.63, 58.46; FAB MS m/z 320 (M+H); Anal. (C$_{18}$H$_{33}$N$_5$.5HBr. 0.5HOAc. 1.7H$_2$O); Calc. C, 29.08; H, 5.57; N, 8.92; Br 50.91. Found C, 29.04; H, 5.60; N, 8.73; Br, 50.87.

EXAMPLE 22

1-[2-Methylpyrid-4-yl(methylene)]-1,4,8,11-tetraazacyclotetradecane Pentahydrobromide Dihydrate (AMD 7061)

$^1$H NMR (D$_2$O) δ 2.01–2.08 (m, 2H), 2.22 (m, 2H), 2.70–2.72 (m, 2H), 2.77 (s, 3H), 2.91–2.92 (m, 2H), 3.33–3.52 (m, 12H), 4.00 (s, 2H), 7.86–7.89 (m, 2H), 8.56 (d, 1H, J=5.7 Hz); FAB MS r/z 306 (M+H); Anal. (C$_{17}$H$_{31}$N$_5$.4.9HBr.0.3HOAc.2.1H$_2$O); Calc. C, 27.9; H, 5.49; N, 9.24; Br, 51.67. Found C, 28.08; H, 5.50; N, 9.56; Br, 51.56.

EXAMPLE 23

1-[2,6-Dichloropyrid-4-yl(methylene)-]4,8,11-tetraazacyclotetradecane Trihydrochloride Bishydrate (AMD 3451)

$^1$H NMR (D$_2$O) δ 1.83–1.88 (m, 2H), 2.04–2.08 (m, 2H), 2.58–2.62 (m, 2H), 2.79–2.81 (m, 2H), 3.12–3.44 (m, 12H), 3.69 (s, 2H), 7.30 (s, 2H); $^{13}$C NMR (D$_2$O) □□36.26, 37.69, 55.26, 56.18, 58.33, 58.56, 58.92, 59.23, 63.57, 65.44, 70.72, 140.37, 166.14, 167.37; FAB MS m/z 360 (M+H). Anal. (C$_{16}$H$_{34}$N$_5$Cl$_5$O$_2$): Calc. C, 38.00; H, 6.78; N, 13.85; Cl, 35.05. Found: C, 38.33; H, 6.42; N, 13.88; Cl, 35.43.

EXAMPLE 24

1-[2-Chloropyrid-5-yl(methylene)]-1,4,8,11-tetraazacyclotetradecane Tetrahydrochloride Hemihydrate (AMD 3454)

$^1$H NMR (D$_2$O) δ 1.96–2.09 (br m, 4H), 3.02–3.17 (m, 4H), 3.19–3.28 (br m, 8H), 3.40 (s, 4H), 4.10 (s, 2H), 7.40 (d, 1H, J=8.2 Hz), 7.80 (d, 1H, J=8.2 Hz), 8.27 (s, 1H); $^{13}$C NMR(D$_2$O) δ 19.36, 19.47, 38.17, 38.64, 39.06, 41.74, 41.88, 42.18, 45.66, 48.29, 54.62, 125.59, 126.69, 142.79, 150.77, 151.75; FAB-MS m/z 326 (M+H). Anal. Calcd for C$_{16}$H$_{28}$N$_5$Cl0.4HCl.0.5H$_2$O: C, 39.98; H, 6.92; N, 14.57; Cl, 36.87. Found: C, 40.36; H, 7.06; N, 14.56; Cl, 36.92.

General Procedures A, B and C were used to prepare the following compounds:

EXAMPLE 25

N-[1,4,8,11-Tetraazacyclotetradecanyl-1,4-phenylenebis (methylene)]-purine Pentahydrobromide DiHydrate (AMD 3472)

$^1$H NMR (D$_2$O) δ 1.88–2.05 (br m, 4H), 3.06–3.22 (br m, 8H), 3.27–3.44 (br m, 8H), 4.22 (s, 2H), 5.59 (s, 2H), 7.29 (s, 4H), 8.80 (s, 1H), 9.11 (s, 1H), 9.28 (s, 1H); $^{13}$C NMR (D$_2$O) δ 18.39, 19.25, 37.24, 37.55, 37.71, 41.13, 41.37, 41.71, 44.41, 47.73, 54.87, 129.45, 131.81, 132.53, 136.67, 140.96, 147.88, 152.46, 154.37; FAB-MS m/z 423 (M+H). Anal. Calcd for C$_{23}$H$_{34}$N$_8$.5HBr.H$_2$O.0.5CH$_3$CO$_2$H: C, 32.27; H, 5.07; N, 12.54; Br, 44.73. Found: C, 32.66; H, 4.81; N, 12.41; Br, 44.58.

EXAMPLE 26

1-[1,4,8,11-Tetraazacyclotetradecanyl-1,4-phenylenebis (methylene]-4 phenylpiperazine Pentahydrobromide Hydrate (AMD 3526)

$^1$H NMR (D$_2$O) δ 1.88–2.06 (br m, 4H), 3.11–3.53 (br m, 24H), 4.30 (s, 2H), 4.32 (s, 2H), 6.89–6.97 (m, 3H), 7.19–7.24 (m, 2H), 7.49 (s, 4H); $^{13}$C NMR (D$_2$O) δ 18.74, 19.37, 37.34, 41.47, 41.76, 42.03, 44.31, 47.45, 48.26, 51.16, 58.48, 59.29, 118.18, 122.34, 129.99, 130.37, 131.53, 131.85, 132.62, 148.47; FAB-MS m/z 547 (M+H$^{81}$Br), 545 (M+H$^{79}$Br), 465 (M+H). Anal. Calcd for C$_{28}$H$_{44}$N$_6$. 5HBr. H$_2$O: C, 37.90; H, 5.79; N, 9.47; Br, 45.03. Found: C, 37.72; H, 5.98; N, 9.38; Br, 46.78.

TABLE 4

| Compound | IC$_{50}$$^a$ (μg/mL) |
| --- | --- |
| AMD3451 | 8.9 |
| AMD3472 | 45.4 |
| AMD3454 | 32.3 |
| AMD3526 | 82 |
| AMD3100 | >100 |

$^a$50% Inhibitory Concentration (IC$_{50}$)(μg/mL) exhibited by AMD compounds against infection of U87.CD4.CCR5 by HIV-1 BaL The active compounds may be administered in the form of a pharmaceutical composition formulated according to well known principles and incorporating the compound, preferably in unit dose form, in combination with a pharmaceutically acceptable diluent, carrier or excipient. Such compositions may be in the form of solutions or suspensions for injection, or irrigation or be in capsule, tablet, dragee, or other solid composition or as a solution or suspension for oral administration or formulated into pessaries or suppositories or sustained release forms of any of the above for implantation. Suitable diluents, carriers, excipients and other components are well known. It may be desirable also to formulate a composition for topical administration such as an ointment or cream. The compounds of the invention may be used, in the form of a composition or alone.

The pharmaceutical compositions according to the invention may be formulated in unit dosages determined in accordance with conventional pharmacological methods, suitably to provide active compounds in the dosage range in humans of from 0.1 to 100 mg/kg body weight per day, in a single dose or in a number of smaller doses. Preferred dosage ranges are 1 to 30 mg/kg body weight per day intravenous (iv) or intraperitoneal (ip). Other active compounds may be used in the compositions or such active compounds or supplemental therapy may be included in a course of treatment. The pharmaceutical compositions are useful for treatment of a patient comprising an effective therapeutic amount of the novel compound, where said compound effectively binds to a chemokine receptor.

The present invention further contemplates the use of these compositions in the manufacture of a medicament for the treatment of HIV-infected patients and/or the treatment of a disease by the regulation of endothelial cell function and/or the treatment of a disease relating to vascularization of the gastrointestinal tract; haematopoiesis; or cerebellar development.

In a method for treating a patient infected with HIV, the pharmaceutical composition is administered to said patient as a therapeutically effective amount of a pharmaceutical composition in a pharmaceutically acceptable carrier. In a method of treating a patient with a disease related to the regulation of endothelial cell function, the pharmaceutical composition is administered to said patient as a therapeutically effective amount of a pharmaceutical composition in a pharmaceutically acceptable carrier. The present invention further contemplates methods of treating a patient with a disease relating to vascularization of the gastrointestinal tract; haematopoiesis; or cerebellar development, by administering to said patient a therapeutically effective amount of a pharmaceutical composition in a pharmaceutically acceptable carrier.

The present invention further contemplates a method of treating a patient with a disease relating to basal leukocyte trafficking or the extravasation and tissue infiltration of leukocytes in response to inciting antigens, by administering to said patient a therapeutically effective amount of a pharmaceutical composition in a pharmaceutically acceptable carrier. The present method also contemplates treating a patient, by administering to said patient a therapeutically effective amount of a pharmaceutical composition in a pharmaceutically acceptable carrier, wherein said compound effectively binds to a chemokine receptor.

What is claimed is:

1. A compound of general formula I,

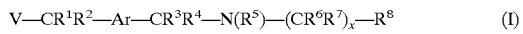

$$V-CR^1R^2-Ar-CR^3R^4-N(R^5)-(CR^6R^7)_x-R^8 \qquad (I)$$

wherein V is an optionally substituted 1,4,7-triazacyclotetra-decanyl or a 4,7,10-triazabicyclo[13.3.1]heptadeca-1(17),13,15-trienyl system, optionally substituted by hydroxyl, alkoxy, thiol, thioalkyl, halogen, nitro, carboxy, carboxyamido, sulfonate and/or phosphate;

$R^1$ to $R^7$ may be the same or different and are independently selected from hydrogen or straight, branched or cyclic $C_{1-6}$ alkyl;

$R^8$ is pyridyl, pyrimidinyl, pyrazinyl, imidazolyl, thiophene-yl, thiophenyl, aminobenzyl, piperidinyl, piperazinyl or mercaptan;

Ar is a phenylene ring optionally substituted at single or multiple positions with alkyl, aryl, amino, alkoxy, hydroxy, halogen, carboxyl and/or carboxamido; and x is 1 or 2;

and the acid addition salts and metal complexes thereof.

2. A compound of claim 1, which is:

N-[4-(1,4,7-Triazacyclotetra-decanyl)-1,4-phenylenebis(methylene)]-2-(aminomethyl)pyridine (AMD 7049);

N-[7-(4,7,10,17-Tetraazabicyclo[13.3.1]heptadeca-1(17),13,15-trienyl)-1,4-phenylenebis(methylene)]-2-(aminomethyl)pyridine (AMD 7051);

N-[7-(4,7,10-Triazabicyclo[13.3.1]heptadeca-1 (17),13,15-trienyl)-1,4-phenylenebis(methylene)]-2-(aminomethyl)pyridine (AMD 7058); or N-[1-(1,4,7-Triazacyclotetra-decanyl)-1,4-phenylenebis(methylene)]-2-(aminomethyl)pyridine (AMD 7059); and the acid addition salts and metal complexes thereof.

3. A pharmaceutical composition comprising an effective therapeutic amount of claim 1 or 2 along with a pharmaceutically acceptable carrier.

4. A composition according to claim 3, unit dosage form.

5. A method of treating a patient infected with HIV, which method comprises administering to said patient a therapeutically effective amount of a pharmaceutical composition of claim 3.

6. A method of treating a patient with a disease characterized by abnormalities in vascularization of the gastrointestinal tract, which method comprises administering to said patient a therapeutically effective amount of a pharmaceutical composition of claim 3.

7. A method of treating a patient with a disease characterized by abnormalities in the extravasation and tissue infiltration of leukocytes in response to inciting antigens, which method comprises administering to said patient a therapeutically effective amount of a pharmaceutical composition of claim 3.

* * * * *